United States Patent
Im et al.

(10) Patent No.: US 12,122,999 B2
(45) Date of Patent: Oct. 22, 2024

(54) COMPOSITION FOR PREVENTING OR TREATING COGNITIVE DYSFUNCTION INCLUDING INHIBITOR OR MECP2 EXPRESSION

(71) Applicant: KOREA INSTITUTE OF SCIENCE AND TECHNOLOGY, Seoul (KR)

(72) Inventors: Heh-In Im, Seoul (KR); Sangjoon Lee, Seoul (KR); Ji Eun Choi, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 13 days.

(21) Appl. No.: 17/745,416

(22) Filed: May 16, 2022

(65) Prior Publication Data
US 2023/0075981 A1    Mar. 9, 2023

(30) Foreign Application Priority Data

Sep. 6, 2021    (KR) .................. 10-2021-0118530

(51) Int. Cl.
*C12N 15/113*    (2010.01)
*A61P 25/28*    (2006.01)

(52) U.S. Cl.
CPC ............ *C12N 15/113* (2013.01); *A61P 25/28* (2018.01); *C12N 2310/14* (2013.01); *C12N 2310/531* (2013.01)

(58) Field of Classification Search
CPC .. A61K 48/00; C12N 15/113; C12N 2310/14; C12N 2310/531; A61P 25/28
See application file for complete search history.

(56) References Cited

U.S. PATENT DOCUMENTS

| | | | |
|---|---|---|---|
| 2010/0247543 A1* | 9/2010 | Maes ................ | A61K 31/7105 514/23 |
| 2018/0044673 A1* | 2/2018 | Zoghbi ............. | A61K 31/7125 |
| 2020/0060994 A1* | 2/2020 | Fainzilber ............. | A61K 45/06 |

FOREIGN PATENT DOCUMENTS

| KR | 10-2018-0032251 A | 3/2018 | |
|---|---|---|---|
| WO | WO-2020212448 A1 * | 10/2020 | ........... A61K 48/005 |
| WO | WO-2020257194 A1 * | 12/2020 | ........... A61K 9/0085 |

OTHER PUBLICATIONS

Moore et al., Short Hairpin RNA (shRNA): Design, Delivery, and Assessment of Gene Knockdown, Methods Mol Biol., 629, pp. 141-158 (Year: 2010).*
Reichwald et al., Comparative sequence analysis of the MECP2-locus in human and mouse reveals new transcribed regions, Mammalian Genome, 11, pp. 182-190 (Year: 2000).*

(Continued)

*Primary Examiner* — Neil P Hammell
*Assistant Examiner* — Shabana S Meyering
(74) *Attorney, Agent, or Firm* — NSIP Law

(57) ABSTRACT

Disclosed is a composition for preventing or treating a degenerative brain disease. The composition includes, as an active ingredient, a MECP2 inhibitor for treating the degenerative brain disease, a polynucleotide encoding the MECP2 inhibitor or a recombinant virus containing the MECP2 inhibitor. The composition is useful for the treatment of a degenerative brain disease (particularly Alzheimer's syndrome) caused by beta-amyloid. In addition, the composition is effective in improving or ameliorating deterioration of cognitive functions and social deficits caused by Alzheimer's syndrome.

3 Claims, 17 Drawing Sheets

Specification includes a Sequence Listing.

(56) References Cited

OTHER PUBLICATIONS

Brito et al., MeCP2 gates spatial learning-induced alternative splicing events in the mouse hippocampus, Mol Brain, pp. 13:156 (Year: 2020).*
Deng et al.,MeCP2 in the nucleus accumbens contributes to neural and behavioral responses to psychostimulants, Nat Neurosci., 13, pp. 1128-1136 (Year: 2010).*
Lee et al., MeCP2 regulates gene expression through recognition of H3K27me3, Nat Commun., 11 (1), 3140, p. 15 (Year: 2020).*
Maphis, Nicole M., et al. "Whole Genome Expression Analysis in a Mouse Model of Tauopathy Identifies MECP2 as a Possible Regulator of Tau Pathology." Frontiers in Molecular Neuroscience 10, Mar. 17, 2017, (13 pages).

* cited by examiner

FIG. 5
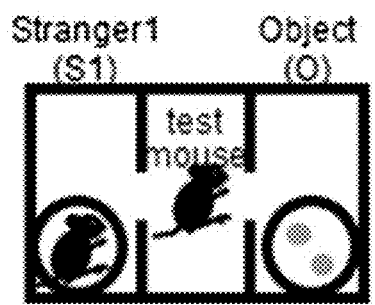
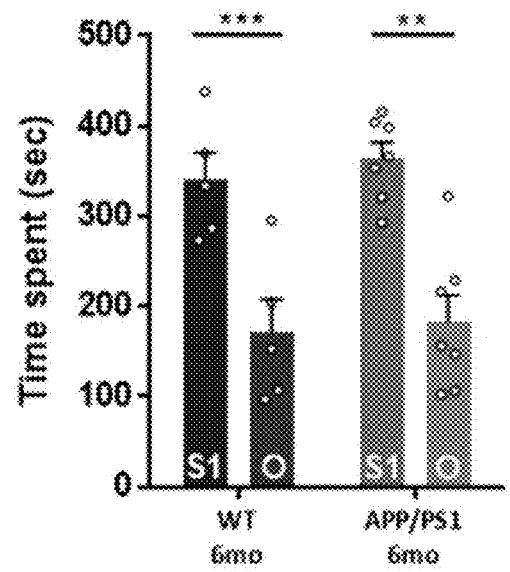

FIG. 6
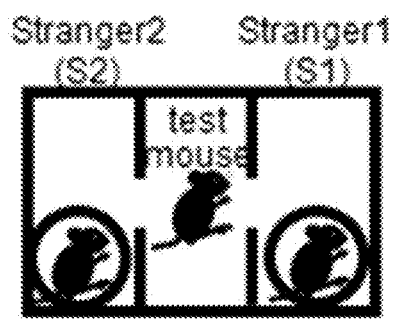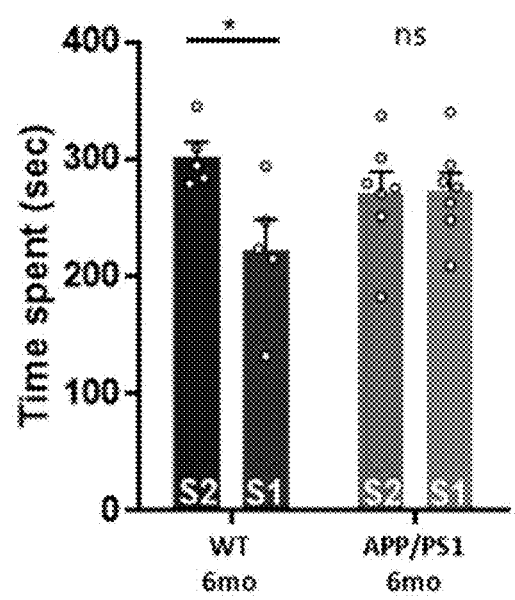

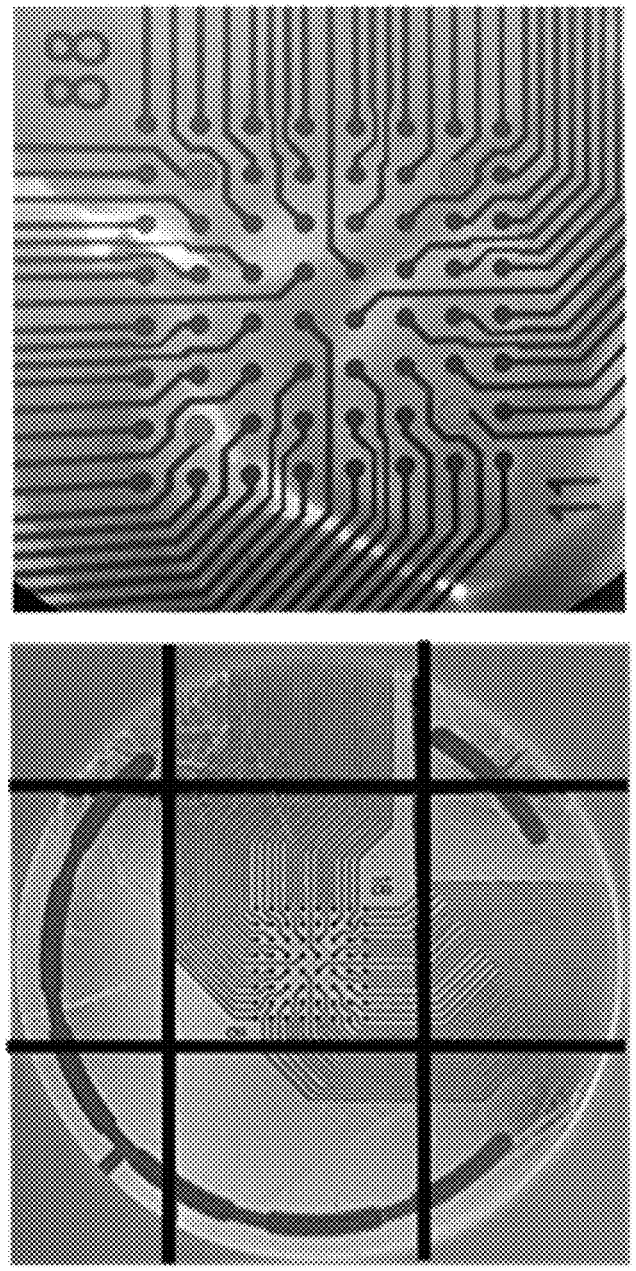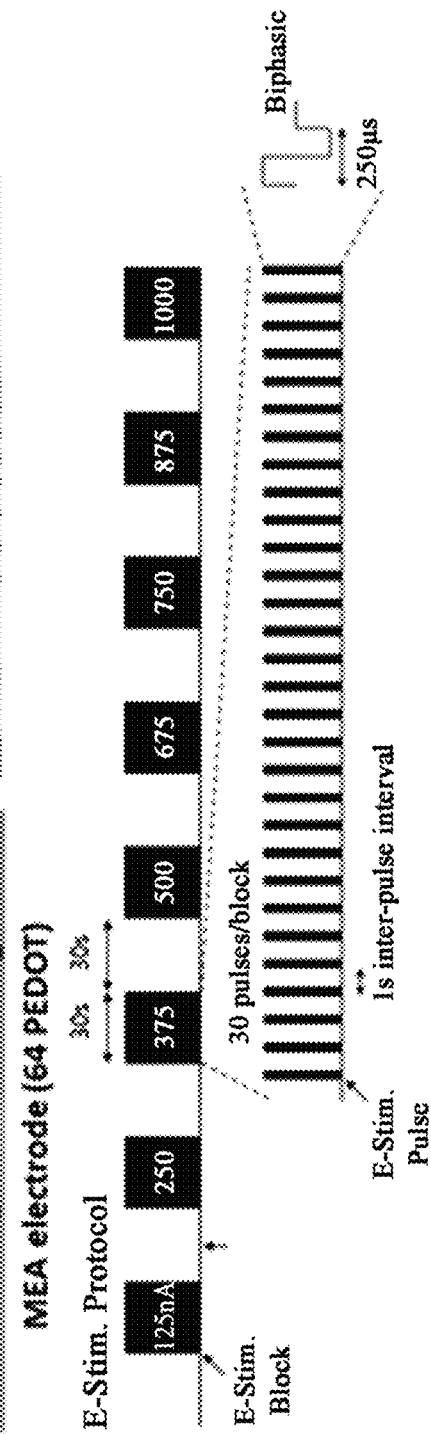
FIG. 15

SEQUENCE LISTING

```
<160> NUMBER OF SEQ ID NOS: 6

<210> SEQ ID NO 1
<211> LENGTH: 484
<212> TYPE: PRT
<213> ORGANISM: Artificial Sequence
<220> FEATURE:
<223> OTHER INFORMATION: MECP2

<400> SEQUENCE: 1
```

```
Met Val Ala Gly Met Leu Gly Leu Arg Glu Glu Lys Ser Glu Asp Gln
1               5                   10                  15

Asp Leu Gln Gly Leu Arg Asp Lys Pro Leu Lys Phe Lys Lys Ala Lys
            20                  25                  30

Lys Asp Lys Lys Glu Asp Lys Glu Gly Lys His Glu Pro Leu Gln Pro
        35                  40                  45

Ser Ala His His Ser Ala Glu Pro Ala Glu Ala Gly Lys Ala Glu Thr
50                      55                  60

Ser Glu Ser Ser Gly Ser Ala Pro Ala Val Pro Glu Ala Ser Ala Ser
65                      70              75                  80

Pro Lys Gln Arg Arg Ser Ile Ile Arg Asp Arg Gly Pro Met Tyr Asp
                85                  90                  95

Asp Pro Thr Leu Pro Glu Gly Trp Thr Arg Lys Leu Lys Gln Arg Lys
            100                 105                 110

Ser Gly Arg Ser Ala Gly Lys Tyr Asp Val Tyr Leu Ile Asn Pro Gln
        115                 120                 125

Gly Lys Ala Phe Arg Ser Lys Val Glu Leu Ile Ala Tyr Phe Glu Lys
    130                 135                 140

Val Gly Asp Thr Ser Leu Asp Pro Asn Asp Phe Asp Phe Thr Val Thr
145                 150                 155                 160

Gly Arg Gly Ser Pro Ser Arg Arg Glu Gln Lys Pro Pro Lys Lys Pro
                165                 170                 175

Lys Ser Pro Lys Ala Pro Gly Thr Gly Arg Gly Arg Gly Arg Pro Lys
            180                 185                 190

Gly Ser Gly Thr Gly Arg Pro Lys Ala Ala Ser Glu Gly Val Gln
            195                 200                 205

Val Lys Arg Val Leu Glu Lys Ser Pro Gly Lys Leu Val Val Lys Met
210                 215                 220

Pro Phe Gln Ala Ser Pro Gly Lys Gly Glu Gly Gly Gly Ala Thr
225                 230                 235                 240

Thr Ser Ala Gln Val Met Val Ile Lys Arg Pro Gly Arg Lys Arg Lys
            245                 250                 255

Ala Glu Ala Asp Pro Gln Ala Ile Pro Lys Lys Arg Gly Arg Lys Pro
            260                 265                 270

Gly Ser Val Val Ala Ala Ala Ala Glu Ala Lys Lys Lys Ala Val
    275                 280                 285

Lys Glu Ser Ser Ile Arg Ser Val His Glu Thr Val Leu Pro Ile Lys
    290                 295                 300

Lys Arg Lys Thr Arg Glu Thr Val Ser Ile Glu Val Lys Glu Val Val
305                 310                 315                 320

Lys Pro Leu Leu Val Ser Thr Leu Gly Glu Lys Ser Gly Lys Gly Leu
            325                 330                 335

Lys Thr Cys Lys Ser Pro Gly Arg Lys Ser Lys Glu Ser Ser Pro Lys
        340                 345                 350

Gly Arg Ser Ser Ser Ala Ser Ser Pro Pro Lys Lys Glu His His His
        355                 360                 365

His His His His Ser Glu Ser Thr Lys Ala Pro Met Pro Leu Leu Pro
    370                 375                 380

Ser Pro Pro Pro Glu Pro Glu Ser Ser Glu Asp Pro Ile Ser Pro
385                 390                 395                 400

Pro Glu Pro Gln Asp Leu Ser Ser Ile Cys Lys Glu Glu Lys Met
                405                 410                 415
```

Pro Arg Gly Gly Ser Leu Glu Ser Asp Gly Cys Pro Lys Glu Pro Ala
              420                 425                 430

Lys Thr Gln Pro Met Val Ala Thr Thr Thr Val Ala Glu Lys Tyr
        435                 440                 445

Lys His Arg Gly Glu Gly Glu Arg Lys Asp Ile Val Ser Ser Met
    450                 455                 460

Pro Arg Pro Asn Arg Glu Glu Pro Val Asp Ser Arg Thr Pro Val Thr
465                 470                 475                 480

Glu Arg Val Ser

<210> SEQ ID NO 2
<211> LENGTH: 1455
<212> TYPE: DNA
<213> ORGANISM: Artificial Sequence
<220> FEATURE:
<223> OTHER INFORMATION: MECP2

<400> SEQUENCE: 2

| | | | | | |
|---|---|---|---|---|---|
| atggtagctg | ggatgttagg | gctcagggag | gaaaagtcag | aagaccagga | tctccaggggc | 60 |
| ctcagagaca | agccactgaa | gtttaagaag | gcgaagaaag | acaagaagga | ggacaaagaa | 120 |
| ggcaagcatg | agccactaca | accttcagcc | caccattctg | cagagccagc | agaggcaggc | 180 |
| aaagcagaaa | catcagaaag | ctcaggctct | gccccagcag | tgccagaagc | ctcggcttcc | 240 |
| cccaaacagc | ggcgctccat | tatccgtgac | cggggaccta | tgtatgatga | ccccaccttg | 300 |
| cctgaaggtt | ggacacgaaa | gcttaaacaa | aggaagtctg | gccgatctgc | tggaaagtat | 360 |
| gatgtatatt | tgatcaatcc | ccagggaaaa | gcttttcgct | ctaaagtaga | attgattgca | 420 |
| tactttgaaa | aggtgggaga | cacctccttg | gaccctaatg | attttgactt | cacggtaact | 480 |
| gggagaggga | gcccctccag | gagagagcag | aaaccaccta | gaagcccaaa | tctcccaaa | 540 |
| gctccaggaa | ctggcagggg | tcgggacgc | cccaagggga | gcggcactgg | agaccaaag | 600 |
| gcagcagcat | cagaaggtgt | tcaggtgaaa | agggtcctgg | agaagagccc | tgggaaactt | 660 |
| gttgtcaaga | tgccttttcca | agcatcgcct | gggggtaagg | gtgagggagg | tggggctacc | 720 |
| acatctgccc | aggtcatggt | gatcaaacgc | cctggcagaa | agcgaaaagc | tgaagctgac | 780 |
| ccccaggcca | ttcctaagaa | acggggtaga | aagcctggga | gtgtggtggc | agctgctgca | 840 |
| gctgaggcca | aaaagaaagc | cgtgaaggag | tcttccatac | ggtctgtgca | tgagactgtg | 900 |
| ctccccatca | gaagcgcaa | gacccgggag | acggtcagca | tcgaggtcaa | ggaagtggtg | 960 |
| aagcccctgc | tggtgtccac | ccttggtgag | aaaagcggga | agggactgaa | gacctgcaag | 1020 |
| agccctgggc | gtaaaagcaa | ggagagcagc | cccaagggc | gcagcagcag | tgcctcctcc | 1080 |
| ccacctaaga | aggagcacca | tcatcaccac | catcactcag | agtccacaaa | ggcccccatg | 1140 |
| ccactgctcc | catcccaccc | ccacctgag | cctgagagct | ctgaggaccc | catcagcccc | 1200 |
| cctgagcctc | aggacttgag | cagcagcatc | tgcaaagaag | agaagatgcc | ccgaggaggc | 1260 |
| tcactggaaa | gcgatggctg | ccccaaggag | ccagctaaga | ctcagcctat | ggtcgccacc | 1320 |
| actaccacag | ttgcagaaaa | gtacaaacac | cgaggggagg | gagagcgcaa | agacattgtt | 1380 |
| tcatcttcca | tgccaaggcc | aaacagagag | gagcctgtgg | acagccggac | gcccgtgacc | 1440 |
| gagagagtta | gctga | | | | | 1455 |

<210> SEQ ID NO 3
<211> LENGTH: 19
<212> TYPE: DNA
<213> ORGANISM: Artificial Sequence

```
<220> FEATURE:
<223> OTHER INFORMATION: shMeCP2

<400> SEQUENCE: 3
tgagccacta caaccttca                                               19

<210> SEQ ID NO 4
<211> LENGTH: 19
<212> TYPE: DNA
<213> ORGANISM: Artificial Sequence
<220> FEATURE:
<223> OTHER INFORMATION: shMeCP2

<400> SEQUENCE: 4
gagcggattg caaagcaaa                                               19

<210> SEQ ID NO 5
<211> LENGTH: 19
<212> TYPE: DNA
<213> ORGANISM: Artificial Sequence
<220> FEATURE:
<223> OTHER INFORMATION: shMeCP2

<400> SEQUENCE: 5
aggacagatg cagacctaa                                               19

<210> SEQ ID NO 6
<211> LENGTH: 19
<212> TYPE: DNA
<213> ORGANISM: Artificial Sequence
<220> FEATURE:
<223> OTHER INFORMATION: shMeCP2

<400> SEQUENCE: 6
tccactgcta cttacttgg                                               19
```

COMPOSITION FOR PREVENTING OR TREATING COGNITIVE DYSFUNCTION INCLUDING INHIBITOR OR MECP2 EXPRESSION

CROSS-REFERENCE TO RELATED APPLICATIONS

This application claims priority under 35 U.S.C. § 119 to Korean Patent Application No. 10-2021-0118530 filed on Sep. 6, 2021 in the Korean Intellectual Property Office, the disclosure of which is incorporated herein by reference in its entirety.

REFERENCE TO AN ELECTRONIC SEQUENCE LISTING

The contents of the electronic sequence listing ("NTCR20220524_0211410002_SequenceListing.txt"; size is 7 KB (kilobytes) and it was created on Jun. 9, 2022) is herein incorporated by reference in its entirety.

BACKGROUND OF THE INVENTION

1. Field of the Invention

The present invention relates to a composition for preventing or treating cognitive dysfunction by inhibiting MECP2 expression or activity. More specifically, the present invention relates to a composition for preventing or treating cognitive dysfunction or a psychiatric disorder associated with cognitive dysfunction including a MECP2 inhibitor as an active ingredient and a method for screening substances for the prevention or treatment of cognitive dysfunction or a psychiatric disorder associated with cognitive dysfunction.

2. Description of the Related Art

Cognitive dysfunction characterized by a loss of cognitive functional ability can be divided into dementia and mild cognitive impairment. Mild cognitive impairment is a condition in which a person complains of subjective memory impairment or has an abnormality found on objective testing but the subjective memory impairment or abnormality is not severe enough to interfere with his/her normal daily life and his/her mental function is maintained normal. Accordingly, mild cognitive impairment is not considered dementia. Apoptosis of neurons already occurs in the brain before the onset of mild cognitive impairment and there are no symptoms yet in this stage, making it difficult to distinguish mild cognitive impairment from memory impairment caused by normal aging. Mild cognitive impairment is more common than dementia and accounts for 15-30% of the population over 60 years old. This proportion increases with age. Mild cognitive impairment is a state between normal aging and Alzheimer's disease and approximately 15% of patients with mild cognitive impairment develop dementia symptoms every year. The number of dementia patients worldwide is expected to exceed 100 million in 2050, which is 3.1 times that of 2013. South Korea is a super-aging society in which the share of the population over age 65 exceeds 20% of the total population and the number of dementia patients in South Korea is expected to increase most rapidly in the world. Thus, dementia is emerging as a major social issue in South Korea.

Extensive and numerous studies have been conducted thus far on the causes of and therapies for cognitive dysfunction such as dementia. However, efforts to find the causes of cognitive dysfunction and develop effective therapies for cognitive dysfunction are still in early stages. Tacrine, rivastigmine, galantamine, donepezil, and memantine have been approved as therapeutic agents for Alzheimer's dementia as cognitive dysfunction by the U.S. FDA. However, currently available therapeutic agents for dementia only temporarily relieve the progression or symptoms of dementia instead of providing treatment for dementia. Moreover, these drugs lose their effects as apoptosis of neurons develops and have no effect on severe dementia. Most of these drugs are anti-inflammatories, cause side effects such as hepatotoxicity and damage to the mucous membrane of the digestive organs, and are limited to symptomatic therapies rather than ultimate treatment of causes.

Many pharmaceutical companies have spurred research efforts to develop drugs for cognitive dysfunction. Although new drug development will bring huge economic and social profits, the enormous development cost makes it difficult for pharmaceutical companies to hesitate to develop new drugs.

PRIOR ART DOCUMENTS

Patent Documents

Patent Document 1. Korean Patent Publication No. 10-2018-0032251

SUMMARY OF THE INVENTION

The present invention has been made in an effort to solve the above-described problems and one object of the present invention is to provide a pharmaceutical composition for preventing or treating cognitive dysfunction.

A further object of the present invention is to provide a pharmaceutical composition for preventing or treating a psychiatric disorder associated with cognitive dysfunction.

Another object of the present invention is to provide a method for screening substances for the prevention or treatment of cognitive dysfunction.

Another object of the present invention is to provide a method for screening substances for the prevention or treatment of a psychiatric disorder associated with cognitive dysfunction.

Another object of the present invention is to provide a method for treating cognitive dysfunction or a psychiatric disorder associated with cognitive dysfunction by administering the composition to a human or non-human animal.

Still another object of the present invention is to provide a novel use of an inhibitor of methyl CpG binding protein 2 (MECP2) expression or activity in the manufacture of a medicament for treating cognitive dysfunction or a psychiatric disorder associated with cognitive dysfunction or in the manufacture of a medicament for animal use.

One aspect of the present invention provides a pharmaceutical composition for preventing or treating cognitive dysfunction including an inhibitor of methyl CpG binding protein 2 (MECP2) expression or activity as an active ingredient.

The inhibitor of MECP2 expression or activity may be a nucleic acid molecule selected from the group consisting of siRNAs and shRNAs that bind complementarily to the MECP2 mRNA, or a viral vector containing the nucleic acid molecule.

The shRNA inhibiting MECP2 expression may have the sequence set forth in any one of SEQ ID NOS: 3 to 6.

The viral vector may be selected from the group consisting of retrovirus, adenovirus, adeno-associated virus, herpes simplex virus, lentivirus, and combinations thereof.

The cognitive dysfunction may be a disease selected from the group consisting of learning disability, senile dementia, Lewy body dementia, Alzheimer's dementia, vascular dementia, dementia with Lewy bodies, frontotemporal dementia, Parkinson's disease dementia, Huntington's disease dementia, dementia due to normal pressure hydrocephalus, dementia due to head trauma, mild cognitive impairment, and semantic dementia.

A further aspect of the present invention provides a pharmaceutical composition for preventing or treating a psychiatric disorder associated with cognitive dysfunction including an inhibitor of methyl CpG binding protein 2 (MECP2) expression or activity as an active ingredient.

The psychiatric disorder associated with cognitive dysfunction may be selected from the group consisting of personality change, delusion, hallucination, mood disorder, sleep disorder, change of appetite, altered sexual behavior, psychosis, increased aggression, irritability, nervousness, hostility, depression, anxiety disorder, lethargy, and combinations thereof.

Another aspect of the present invention provides a method for screening candidates for the prevention or treatment of cognitive dysfunction or a psychiatric disorder associated with cognitive dysfunction, including a) treating MECP2 mRNA-expressing cells with test substances and b) selecting the most appropriate ones that reduce the expression level of MECP2 mRNA compared to a control.

The composition of the present invention has the effect of restoring damaged cognitive functions and psychotic symptoms to normal levels due to its ability to inhibit the MECP2 gene. Therefore, the composition of the present invention is effective in preventing or treating cognitive dysfunction and psychiatric disorders induced by cognitive dysfunction.

BRIEF DESCRIPTION OF THE DRAWINGS

These and/or other aspects and advantages of the invention will become apparent and more readily appreciated from the following description of the embodiments, taken in conjunction with the accompanying drawings of which:

FIGS. 5 and 6 show the results of a 3-chamber test (3CT) for APP/PS1 cognitive dysfunction animal models (6 months old) and normal control animal models (6 months old) in Experimental Example 1. Specifically, FIG. 5 shows the degrees of interest of APP/PS1 cognitive dysfunction animal models (6 months old) and normal control animal models (6 months old) in an inanimate object (O) and a live mouse (S1) and FIG. 6 shows the degrees of interest of APP/PS1 cognitive dysfunction animal models (6 months old) and normal control animal models (6 months old) in a familiar mouse (S1) and a novel mouse (S2);

FIG. 11 shows the degrees of interest of experimental animals of Groups 1-3 in Experimental Example 2 in an inanimate object (O) and a live mouse (S1) and FIG. 12 shows the degrees of interest of experimental animals of Groups 1-3 in Experimental Example 2 in a familiar mouse (S1) and a novel mouse (S2);

FIG. 15 schematically shows a microelectrode array (MEA);

DETAILED DESCRIPTION OF THE INVENTION

Figure 1:
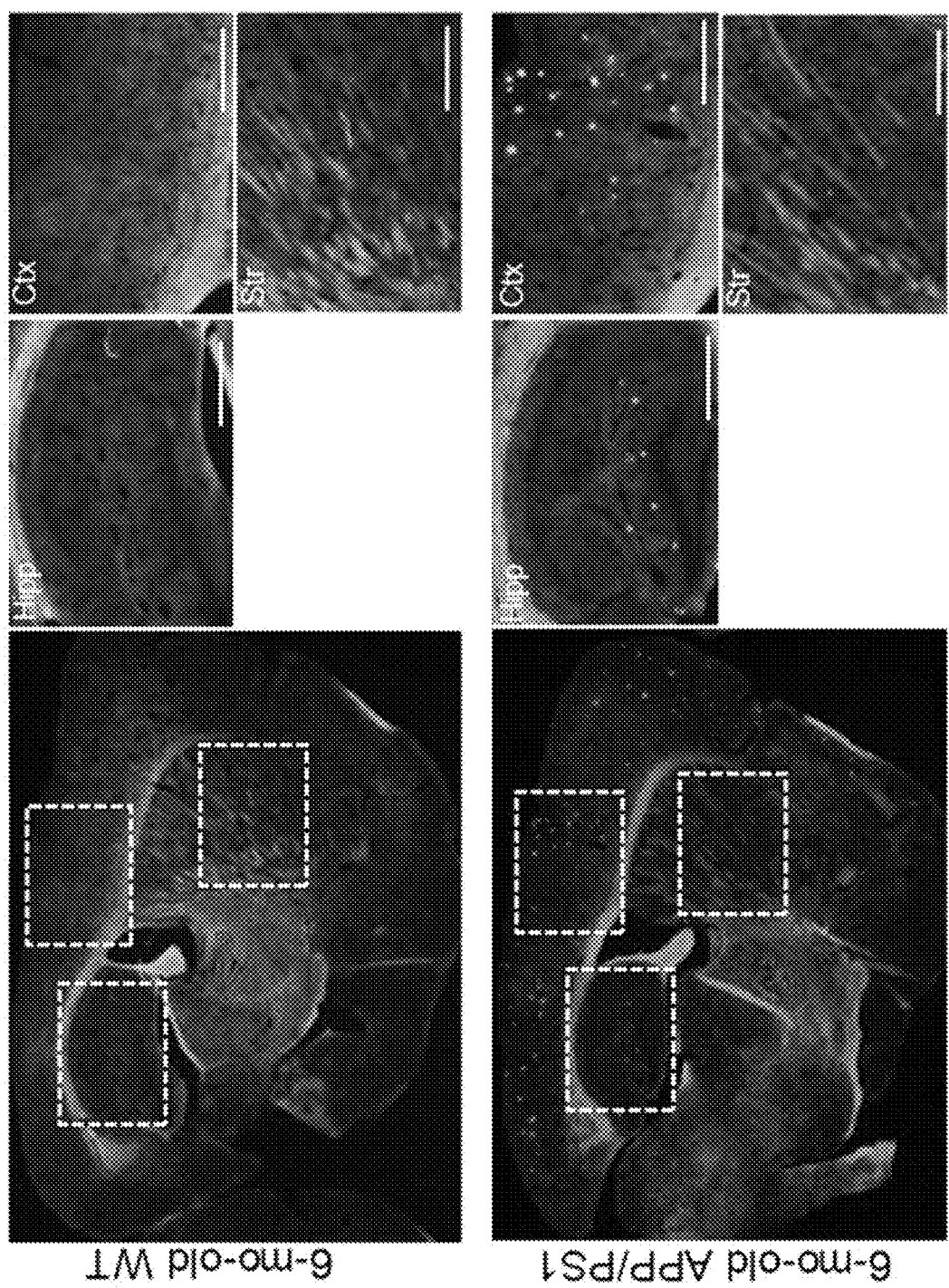
FIG. 1 shows two-photon microscopy images of brain tissue sections from an APP/PS1 cognitive dysfunction animal model (6 months old) and a normal control animal model (6 months old) established in Experimental Example 1 after staining with thioflavin S.

Several aspects and various embodiments of the present invention will now be described in more detail.

One aspect of the present invention is directed to a pharmaceutical composition for preventing or treating cognitive dysfunction including an inhibitor of methyl CpG binding protein 2 (MECP2) expression or activity as an active ingredient.

A further aspect of the present invention is directed to a pharmaceutical composition for preventing or treating a psychiatric disorder associated with cognitive dysfunction, including an inhibitor of methyl CpG binding protein 2 (MECP2) expression or activity as an active ingredient.

Another aspect of the present invention is directed to a pharmaceutical composition for preventing or treating cognitive dysfunction or a psychiatric disorder associated with cognitive dysfunction in an animal, including an inhibitor of methyl CpG binding protein 2 (MECP2) expression or activity as an active ingredient.

Another aspect of the present invention is directed to a method for treating cognitive dysfunction or a psychiatric disorder associated with cognitive dysfunction, including administering the composition to a human or non-human animal.

Another aspect of the present invention is directed to a novel use of an inhibitor of methyl CpG binding protein 2 (MECP2) expression or activity in the manufacture of a medicament for treating cognitive dysfunction or a psychiatric disorder associated with cognitive dysfunction or in the manufacture of a medicament for animal use.

MECP2 is a protein that specifically inhibits the transcription of methylated promoters. The present inventors have analyzed the correlation of the MECP2 protein with cognitive dysfunction and psychiatric disorders associated with cognitive dysfunction, and as a result, found that inhibition of MECP2 expression or activity enables the amelioration, prevention or treatment of the diseases.

The MECP2 protein may be a protein that has substantially the same physiological activity as a protein having the amino acid sequence set forth in SEQ ID NO: 1.

A polynucleotide encoding MECP2 may include a nucleotide sequence encoding the MECP2 protein or a functional equivalent thereof. The nucleotide sequence is intended to include DNA, cDNA, and RNA sequences. Preferably, the MECP2 gene has a nucleotide sequence encoding the amino acid sequence set forth in SEQ ID NO: 1. Most preferably, the MECP2 gene has the nucleotide sequence set forth in SEQ ID NO: 2.

The present invention also provides a siRNA or shRNA that inhibits the expression of MECP2 having the nucleotide sequence set forth in SEQ ID NO: 2. The siRNA or shRNA against MECP2 (SEQ ID NO: 2) can be prepared by any suitable method known to those skilled in the art.

The shRNA inhibiting the expression of MECP2 may have the sequence set forth in any one of SEQ ID NOS: 3 to 6, most preferably the sequence set forth in SEQ ID NO: 3.

The inhibitor of methyl CpG binding protein 2 (MECP2) expression or activity (hereinafter also referred to merely as "MECP2 inhibitor") refers collectively to substances that reduce MECP2 mRNA expression or protein activity. More specifically, the inhibitor of methyl CpG binding protein 2 (MECP2) expression or activity is intended to include all substances that directly act on MECP2 or indirectly act on its ligand or receptor to reduce the expression of MECP2 at a transcriptional level or interfere with the activity of MECP2, resulting in a reduction in the expression or activity of MECP2. The substances inhibiting MECP2 expression may be compounds, nucleic acids, peptides, viruses, and vectors containing the nucleic acids that target MECP2 to inhibit the expression or activity of MECP2, but are not limited to these forms. Examples of substances inhibiting MECP2 expression include antisense oligonucleotides, siRNAs, shRNAs, miRNAs, ribozymes, DNAzymes, and peptide nucleic acids (PNAs) that specifically bind to the MECP2 mRNA to inhibit their expression. Examples of the substances inhibiting MECP2 activity include antibodies and antigen-binding fragments thereof, aptamers, and compounds that specifically bind to the MECP2 protein to inhibit its activity. Preferably, the MECP2 inhibitor is selected from the group consisting of antisense oligonucleotides, siRNAs, and shRNAs that bind complementarily to the MECP2 mRNA.

As used herein, the term "expression inhibition" means to cause a deterioration in the expression of the target gene into mRNA or the translation of the target gene into a protein. Preferably, this term means that the expression of the target gene is at an undetectable or insignificant level.

The antisense oligonucleotide is a DNA, an RNA or a derivative thereof that contains a nucleic acid sequence complementary to a specific mRNA sequence. The antisense oligonucleotide binds to a complementary sequence in an mRNA to effectively inhibit the translation of the mRNA into a protein.

The "small interfering RNA (siRNA)" refers to a short double-stranded RNA molecule that can induce RNA interference through cleavage of a specific mRNA and has a length of 21 to 25 nucleotides. The siRNA may have a double-stranded structure in which a sense strand (a sequence corresponding to the MECP2 mRNA sequence) and an antisense strand (a sequence complementary to the MECP2 mRNA sequence) are located positioned opposite to each other. Alternatively, the siRNA may have a single-stranded structure consisting of self-complementary sense and antisense strands.

The "short hairpin RNA (shRNA)" is a double-stranded RNA that binds complementarily to a specific mRNA, like siRNA, to form a palindromic hairpin structure connected by a loop region, resulting in cleavage of the mRNA. The shRNA overcomes the disadvantages of the siRNA, such as high biosynthesis cost and short-term retention of RNA interference effect due to low cell transfection efficiency. The shRNA is expressed by introduction into cells using a vector system such as retrovirus, adenovirus, adeno-associated virus, herpes simplex virus, lentivirus or plasmid expression vector. Preferably, the shRNA uses a lentiviral, retroviral or adenoviral vector system for expression.

When the MECP2 inhibitor is a siRNA against MECP2, the composition may include an agent that promotes the endocytosis of the siRNA. The agent is generally any of those that promote the endocytosis of nucleic acids. For example, the agent may use liposomes or may be combined with a lipophilic carrier selected from a number of sterols, including cholesterol, cholate, and deoxycholic acid. The agent may be a cationic polymer such as poly-L-lysine, spermine, polysilazane, polyethylenimine (PEI), polydihydroimidazolenium, polyallylamine or chitosan or an anionic polymer such as succinylated PLL, succinylated PEI, polyglutamic acid, polyaspartic acid, polyacrylic acid, polymethacrylic acid, dextran sulfate, heparin or hyaluronic acid.

The present invention also provides a vector that contains the siRNA or shRNA inhibiting the expression of MECP2 having the nucleotide sequence set forth in SEQ ID NO: 2. The vector is composed of a linear DNA, a plasmid DNA, and a recombinant viral vector.

Plasmid is a generic term for non-chromosomal DNA molecules that are capable of replicating and independently proliferating in bacterial cells. Plasmids are ring-shaped. Plasmids are not essential for the survival of bacteria and can be delivered into cells of other species. Using these properties, genetic recombination technology is used in which plasmids are isolated from bacterial cells, digested with restriction enzymes, transfected with a desired gene, introduced into the bacteria, followed by incubation.

The viral vector may be selected from the group consisting of, but not limited to, retrovirus, adenovirus, adeno-associated virus, herpes simplex virus, lentivirus, and combinations thereof. The viral vector is preferably a lentiviral vector.

Adenovirus is a medium-sized (90-100 nm) noneveloped icosohedral virus containing double-stranded DNA. Adenovirus is responsible for 5-10% of upper respiratory diseases in children. Adults are infected with adenovirus as well.

Adeno-associated virus is a single-stranded DNA virus belonging to the family parvoviridae. Adeno-associated virus is a defective virus that cannot replicate itself and can replicate and proliferate only when infected with a helper virus such as an adenovirus, vaccinia or herpesvirus. In the absence of a helper virus, the adeno-associated virus genome is inserted into a specific site on chromosome 19 of a human cell and remains dormant. When infected with a helper virus, the adeno-associated virus genome replicates and proliferates. The adeno-associated virus genome has a 4681 bp DNA with 145 bp ITRs at both ends, which is a minimum nucleotide sequence required for replication, packaging, and rescue. Each ITR contains two ORFs, which the rep gene required for replication and the cap gene encoding a structural protein. Due to its ability to establish latent infections in human cells, adeno-associated virus does not cause any change in cell growth when inserted into the chromosome, can efficiently infect various types of cells, and does not induce an immune response, unlike adenovirus.

The first recombinant adeno-associated virus vector was constructed by deleting the cap gene and inserting a foreign gene, more preferably by replacing the rep and cap genes with foreign genes.

Retrovirus is a group of viruses in which the RNA genome is converted into DNA in an infected cell and the DNA is incorporated into the chromosome of the host cell. Retroviral vectors based on Moloney murine leukemia virus (MoMLV) are currently most widely used in clinical trials for various gene therapies. Retroviral particles have a structure in which a protein core containing double-stranded RNA is surrounded by a lipid envelope. Retroviral infection is initiated by the binding of the envelope protein to a specific receptor on the cell surface. It is known that the receptor for the ecotropic envelope capable of infecting animal cells is a cationic amino acid transporter and the receptor for the MoMLV amphotropic envelope capable of infecting various types of cells is a phosphate transporter (Ram-1). The virus is introduced into cells by fusion with the cell membrane or pinocytosis, and the viral RNA is converted into DNA by reverse transcription and moves to the nucleus. Most retroviruses undergo mitosis and require subsequent destruction of the nuclear membrane in order for the DNA to enter the nucleus. In the nucleus, the DNA is integrated into the chromosome to form a provirus. The gag, pol, and env gene products are synthesized from RNA transcribed from the provirus and they package only genome-sized viral RNAs to produce viral particles.

Lentivirus is a type of retrovirus and can infect not only dividing cells but also cells whose growth has been stopped or whose differentiation has been arrested, unlike normal retroviruses. Due to this ability, lentiviruses are being developed as vectors for gene transfer. A typical example of lentiviral vectors is HIV that contains 6 or more accessary genes in addition to the gag, pol, and env genes. An HIV vector without some accessary genes can infect a wide range of cells such as brain, liver, and muscle cells and can induce continuous gene expression for more than 6 months in animal tests when pseudotyped with the VSV envelope protein.

As used herein, the term "cognitive function" is intended to include various intellectual abilities such as attention, perception, memory, linguistic ability, and executive ability. In view of the purposes of the present invention, the cognitive dysfunction is a concept that can include conditions caused by deterioration of cognitive functions, diseases resulting from the conditions, and all diseases having symptoms of the conditions. Specifically, the cognitive dysfunction may mean a disorder caused by damage to nerve cells in the brain. For example, the cognitive dysfunction may be a disease selected from the group consisting of learning disability, senile dementia, Lewy body dementia, Alzheimer's dementia, vascular dementia, dementia with Lewy bodies, frontotemporal dementia, Parkinson's disease dementia, Huntington's disease dementia, dementia due to normal pressure hydrocephalus, dementia due to head trauma, mild cognitive impairment, and semantic dementia. The cognitive dysfunction is more preferably a disease selected from the group consisting of learning disability, senile dementia, Lewy body dementia, and Alzheimer's dementia.

As used herein, the term "dementia" refers to a syndrome that is caused by acquired deterioration of cognitive functions such as memory, language, and judgment, making it impossible to properly perform daily activities. Progressive and overall deterioration of cognitive functions occurs when brain functions are damaged by various causes compared to when undamaged, leading to significant interference with daily life. Dementia is divided into several dozens of subgroups according to causative diseases. Alzheimer's disease is the most common cause of dementia and accounts for more than 50% of dementia cases. Dementia can be caused by other causative diseases, including degenerative brain diseases such as dementia with Lewy bodies, frontotemporal degeneration, and Parkinson's disease. Accordingly, as the dementia, there can be mentioned senile dementia, Lewy body dementia, Alzheimer's dementia, vascular dementia, dementia with Lewy bodies, frontotemporal dementia, Parkinson's disease dementia, Huntington's disease dementia, dementia due to normal pressure hydrocephalus, dementia due to head trauma, mild cognitive impairment, and semantic dementia.

The cognitive dysfunction is accompanied by various emotional or psychiatric disorders as well as cognitive impairments. Specifically, a group of one or more symptoms selected from the group consisting of personality change, delusion, hallucination, mood disorder, sleep disorder, change of appetite, altered sexual behavior, psychosis, increased aggression, irritability, nervousness, hostility, depression, anxiety disorder, and lethargy is collectively referred to as a behavioral and psychological symptom of dementia (BPSD). Preferably, the psychiatric disorder may be selected from the group consisting of sleep disorder, psychosis, depression, anxiety disorder, lethargy, and combinations thereof.

Psychiatric disorders concomitant with cognitive dysfunction often exhibit short-term and temporary symptoms, unlike major psychiatric disorders. Older drugs such as tricyclic antidepressants are difficult to use for patients with cognitive dysfunction due to their anticholinergic side effects and some of the drugs may aggravate cognitive dysfunction, making their use for psychiatric disorders impossible. That is, psychiatric disorders concomitant with cognitive dysfunction and general psychiatric disorders are phenomenologically identical to each other but may have different causes. Thus, there is an urgent need to develop new therapeutic agents for psychiatric disorders concomitant with cognitive dysfunction. The inhibitor of methyl CpG binding protein 2 (MECP2) expression or activity according to the present invention can ameliorate, prevent or treat accompanying abnormal behaviors (depression and anxiety) in early to severe stages of cognitive dysfunction and has a significant effect on cognitive function. Therefore, the inhibitor of the present invention would be suitable for preventing or treating not only cognitive dysfunction but also psychiatric disorders concomitant with cognitive dysfunction.

In the Examples section that follows, the present inventors have confirmed that MECP2 expression was increased in an animal model with induced cognitive dysfunction due to beta-amyloid overproduction. Particularly, it was confirmed that a considerable number of beta-amyloid plaques were formed in an animal model (APP/PS1) with induced Alzheimer's dementia in the early stage of disease onset (6 months old) due to beta-amyloid overproduction but no deterioration of cognitive functions was observed and only abnormal behaviors (depression and anxiety) such as social deficits appeared. Further, distinct deterioration of cognitive functions was found from the middle stage of disease onset (10 months old).

Thus, the recombinant viral vector containing the shRNA against MECP2 according to the present invention was administered to an animal model with induced cognitive dysfunction to inhibit MECP2 expression. As a result, abnormal behaviors (depression and anxiety) such as social deficits were improved to normal levels, and at the same time, neuronal activity was induced, resulting in enhanced cognitive functions. Therefore, the use of the inhibitor of methyl CpG binding protein 2 (MECP2) expression or activity according to the present invention as an active ingredient is effective in preventing or treating not only cognitive dysfunction but also psychiatric disorders associated with cognitive dysfunction.

As used herein, the term "prevent", "preventing" or "prevention" means all actions that inhibit or delay the development of cognitive dysfunction or a psychiatric disorder associated with cognitive dysfunction or improve, ameliorate or palliate symptoms by administration of the pharmaceutical composition according to the present invention. As used herein, the term "treat", "treating" or "treatment" means all actions that improve, ameliorate, palliate or beneficially change symptoms of the disease by administration of the pharmaceutical composition according to the present invention.

The "pharmaceutical composition", "medicament", "pharmaceutical composition for animal use" or "drug for animal use" may further include a suitable carrier, excipient or diluent known in the art, in addition to the active ingredient.

As used herein, the term "pharmaceutically acceptable" means that the carrier, excipient or diluent is not toxic to cells or humans exposed to the composition. The composition including a pharmaceutically acceptable carrier may be formulated into an oral or parenteral preparation. The pharmaceutical composition may be formulated with diluents or excipients commonly used in the art, such as fillers, extenders, binders, wetting agents, disintegrating agents or surfactants. Examples of suitable carriers, excipients, and diluents include, but are not limited to, lactose, dextrose, sucrose, sorbitol, mannitol, xylitol, erythritol, maltitol, starch, gum acacia, alginate, gelatin, calcium phosphate, calcium silicate, cellulose, methyl cellulose, microcrystalline cellulose, polyvinylpyrrolidone, physiological saline, methyl hydroxybenzoate, propyl hydroxybenzoate, talc, magnesium stearate, mineral oil, dextrin, calcium carbonate, propylene glycol, and liquid paraffin. These components may be added independently or in combination with the inhibitor of methyl CpG binding protein 2 (MECP2) expression or activity as the active ingredient.

The pharmaceutical composition, medicament, pharmaceutical composition for animal use or drug for animal use may be administered by a route commonly used in gene therapy, preferably parenterally. Examples of parenteral routes of administration include intravenous, intraperitoneal, intramuscular, subcutaneous, intracerebral, and topical administration. The pharmaceutical composition, medicament, pharmaceutical composition for animal use or drug for animal use may be administered individually or in combination with other therapeutic agents and may be administered sequentially or simultaneously with conventional therapeutic agents.

Solid preparations for oral administration include tablets, pills, powders, granules, and capsules. Such solid preparations may be prepared by mixing the pharmaceutical composition with at least one excipient, for example, starch, calcium carbonate, sucrose, lactose or gelatin. In addition to the simple excipients, lubricating agents such as magnesium stearate and talc may also be used. Liquid preparations for oral administration are suspensions, solutions for internal use, emulsions, and syrups. The liquid preparations may include various excipients, for example, wetting agents, sweeteners, aromatic substances, and preservatives, as well as simple diluents known in the art, such as water and liquid paraffin. Sterilized aqueous solutions, non-aqueous solvents, suspensions, emulsions, lyophilizates, and suppositories are included in preparations for parenteral administration. The non-aqueous solvents and the suspensions may be propylene glycol, polyethylene glycol, vegetable oils such as olive oil, and injectable esters such as ethyl oleate. Witepsol®, Macrogol (Polyethylene golycol; PEG), Tween™ 61, cacao butter, laurin butter, and glycerogelatin may be used as bases of the suppositories.

The pharmaceutical composition, medicament, pharmaceutical composition for animal use or drug for animal use may be formulated into one or more preparations selected from the group consisting of tablets, pills, powders, granules, capsules, suspensions, solutions for internal use, emulsions, syrups, sterilized aqueous solutions, non-aqueous solvents, lyophilizates, and suppositories.

The pharmaceutical composition, medicament, pharmaceutical composition for animal use or drug for animal use may be administered in a pharmaceutically effective amount. The dose is not particularly limited and may vary depending on a variety of factors, including uptake, patient's weight, age, sex, general health, and diet, time of administration, mode of administration, excretion rate, and severity of the disease. The pharmaceutical composition, medicament, pharmaceutical composition for animal use or drug for animal use is prepared in consideration of its effective amount range. The pharmaceutical composition, medicament, pharmaceutical composition for animal use or drug for animal use may be prepared in unit dosage forms. In this case, the dosage forms may be administered using a specialized dosage regimen according to the judgement of specialists who supervise or observe the administration of drug and individual request or may be administered several times at regular time intervals. The pharmaceutical composition is administered in such an amount that the daily dose of the inhibitor of methyl CpG binding protein 2 (MECP2) expression or activity is preferably 0.005 to 500 mg/kg, more preferably 0.05 to 500 mg. The pharmaceutical composition may be administered in single or divided doses per day.

When the recombinant vector is provided as the active ingredient, it is specifically present in an amount of 0.01 to 500 mg, more specifically 0.1 to 300 mg, but its amount is not limited thereto. When the recombinant virus containing the recombinant vector is provided as the active ingredient, it is specifically present in an amount of $10^3$ to $10^{12}$ IU ($10$ to $10^{10}$ PFU), more specifically $10^5$ to $10^{10}$ IU, but its amount is not limited thereto. When the cells are provided as the active ingredient, they are specifically present in an amount of $10^3$ to $10^8$, more specifically $10^4$ to $10^7$, but its amount is not limited thereto.

The effective dose of the composition according to the present invention is 0.05 to 12.5 mg/kg body weight for the recombinant vector, $10^7$ to $10^{11}$ virus particles ($10^5$ to $10^9$ IU)/kg body weight for the recombinant virus, or $10^3$ to $10^6$/kg body weight for the cells. Specifically, the effective dose of the composition is 0.1 to 10 mg/kg body weight for the recombinant vector, $10^8$ to $10^{10}$ particles ($10^6$ to $10^8$ IU)/kg body weight for the recombinant virus, or $10^2$ to $10^5$/kg body weight for the cells. The composition of the present invention may be administered 2 to 3 times daily. The effective dose is not necessarily limited thereto and may vary depending on the condition of the patient and the severity of the disease.

The amount of the active ingredient may be suitably changed according to the purpose of use (prophylactic, health or therapeutic treatment). The composition of the present invention may be used to prepare a food or beverage. In this case, the inhibitor of methyl CpG binding protein 2 (MECP2) expression or activity is specifically added in an amount of 5% by weight or less, preferably 1% by weight or less, based on the total amount of raw materials. However, the amount of the inhibitor of methyl CpG binding protein 2 (MECP2) expression or activity may be decreased when the food or beverage is taken for a long period of time for health and hygiene or health control. However, the active ingredient may be used in a larger amount because it does not cause any safety problems.

There is no particular restriction on the kind of the food. Examples of foods that may be added with the inhibitor of methyl CpG binding protein 2 (MECP2) expression or activity include meats, sausages, breads, chocolates, candies, snacks, confectionery, pizza, ramens and other noodles, chewing gums, dairy products (including ice creams), soups, beverages, teas, drinks, alcoholic drinks, and vitamin complexes. The food is intended to include all health foods in a general sense.

The food composition of the present invention may be used to prepare a beverage. In this case, the food composition of the present invention may further include various flavoring agents or natural carbohydrates, like general beverages. Examples of the natural carbohydrates include monosaccharides such as glucose and fructose, disaccharides such as maltose and sucrose, natural sweetening agents such as dextrin and cyclodextrin, and synthetic sweetening agents such as saccharin and aspartame. The natural carbohydrates are present in an amount of 0.01 to 10% by weight, preferably 0.01 to 0.1% by weight, based on the total weight of the food composition.

The food composition of the present invention may further include one or more additives selected from nutrients, vitamins, electrolytes, flavoring agents, coloring agents, pectic acid and its salts, alginic acid and its salts, organic acids, protective colloidal thickeners, pH adjusting agents, stabilizers, preservatives, glycerin, alcohols, and carbonating agents for carbonated beverages. The composition of the present invention may further include flesh for the production of a natural fruit juice, fruit juice beverage or vegetable beverage. Such ingredients may be used independently or in combination of two or more.

The amounts of the additives are not limited but are typically in the range of 0.01 to 0.1% by weight, based on the total weight of the food composition of the present invention.

The method for treating cognitive dysfunction or a psychiatric disorder associated with cognitive dysfunction includes administering the composition to a human or non-human animal, particularly a mammal. For example, the composition may be administered to a target subject with cognitive dysfunction or a psychiatric disorder associated with cognitive dysfunction in need of treatment. The composition is preferably administered parenterally.

The dose, mode of administration, and frequency of administration of the composition may be determined by referring to those of the pharmaceutical composition, medicament, pharmaceutical composition for animal use or drug for animal use.

Yet another aspect of the present invention is directed to a method for screening a candidate for the treatment of cognitive dysfunction or a psychiatric disorder associated with cognitive dysfunction, including a) treating cells expressing the MECP2 gene or MECP2 protein with test substances, b) measuring the expression levels of the MECP2 gene, the expression levels of the MECP2 protein or the activities of the MECP2 protein in the treated cells, and c) if any of the test substances is found to reduce the expression level of the MECP2 gene, the expression level of the MECP2 protein or the activity of the MECP2 protein from the measurement results, it is determined to prevent or treat cognitive dysfunction or a psychiatric disorder associated with cognitive dysfunction.

In step (a), test substances to be analyzed are brought into contact with MECP2-exressing cells. The MECP2-exressing cells include cells endogenously expressing MECP2 or cells transiently overexpressing MECP2. The MECP2-expressing cells are preferably brain tissue-derived cells. The test substances refer to unknown substances that are used for screening to determine whether they affect MECP2 expression. For example, the test substances may be antisense oligonucleotides, siRNAs, shRNAs, miRNAs, ribozymes, DNAzymes, PNAs, antibodies, aptamers, natural extracts or synthetic compounds.

In step (b), the expression levels of the MECP2 mRNA or protein and the activities of the MECP2 protein in the cells treated with the test substances are analyzed. The expression levels and activities may be measured and analyzed by reverse transcriptase-polymerase chain reaction, real time-polymerase chain reaction, western blot, northern blot, enzyme linked immunosorbent assay (ELISA), radioimmunoassay (RIA), radioimmunodiffusion, immunoprecipitation assay or immunohistochemical analysis.

In step (c), if any of the test substance is found to reduce or inhibit the expression level of the MECP2 mRNA, the expression level of the MECP2 protein or the activity of the MECP2 protein from the measurement results, it is determined as a therapeutic agent for cognitive dysfunction or a psychiatric disorder associated with cognitive dysfunction.

The present invention will be explained in more detail with reference to the following examples. However, these examples are not to be construed as limiting or restricting the scope and disclosure of the invention. It is to be understood that based on the teachings of the present invention including the following examples, those skilled in the art can readily practice other embodiments of the present invention whose experimental results are not explicitly presented. Such modifications and variations are intended to come within the scope of the appended claims.

The experimental results of the following examples, including comparative examples, are merely representative and the effects of the exemplary embodiments of the present invention that are not explicitly presented hereinafter can be specifically found in the corresponding sections.

Experimental Example 1. Establishment of Animal Models with Cognitive Dysfunction and Normal Control Animal Models In this experiment, 6-month or 10-month-old APP/PS1 mice were used. APP/PS1 mice are Alzheimer's mice genetically mutated to overproduce beta-amyloid (Aβ, β amyloid). The APP/PS1 mice were APPswe/PSEN1dE9 (line 85) mice (The Jackson Lab; available through the JAX MMRRC Stock #034829 (formerly Jackson Lab Stock #004462)) (https://www.alzforum.org/research-models/appswepsen1de9-line-85), which were managed and sold by the Laboratory Animal Resources Center, Korea Institute of Science and Technology (KIST).

Wild-type (WT) mice without genetic mutation for beta-amyloid (Aβ, β amyloid) overproduction were provided from the Laboratory Animal Resources Center, Korea Institute of Science and Technology (KIST) and were used as a normal control group.

The experimental animals were acclimatized to the laboratory environment for at least one week prior to starting the experiment. All mice were housed in cages maintained at a temperature of 22±2° C. and a humidity of 40-60% with a 12-h light/dark cycle and were given water and food ad libitum. All animal procedures were performed in accordance with the Guidelines for Institutional Animal Care and Use Committee of KIST.

Two Groups of Animal Models

Group 1 (APP/PS1): 6-month or 10-month-old APP/PS1 mice genetically mutated to overproduce beta-amyloid (Aβ, β amyloid).

Group 2 (WT): 6-month or 10-month-old normal experimental mice without genetic mutation Experimental Example 2. Establishment of MeCP2 Knockdown Dementia Animal Models (APPPS1+shMeCP2)

pGFP-C-shLenti-MeCP2 shRNA vector (ORIGENE) expressing the shRNA (SEQ ID NO: 3: 5'-TGAGCCAC-TACAACCTTCA-3') against the MeCP2 gene (SEQ ID NO: 2) and pGFP-C-shLenti-non-targeting shRNA control vector (TR30021) expressing a shRNA with a random sequence at a specific region as a negative control were purchased from ORIGENE (USA).

Lentiviruses expressing the shRNA against MeCP2 or the control shRNA were produced using the vector, a third-generation packaging system (pMDLg/pRRE, pRSV-Rev, pMD2.G), and HEK293T cell line according to the manufacturer's manual. The HEK293T cell culture medium containing the lentiviruses was concentrated by ultracentrifugation at 50,000 g at 4° C. for 90 min. Thereafter, the titer of the lentivirus concentrate was determined using the Lenti-X™ p24 Rapid Titer Kit (Clontech, USA).

The recombinant lentiviruses ($2 \times 10^6$ transduction units/ml) were introduced into the striatum of the cognitive dysfunction animal models (APP/PS1) (10 months old) to establish MeCP2 knockdown dementia animal models (APP/PS1+shMeCP2). For injection, a Nanofil 33 G blunt needle, a Nanofil syringe (World Precision Instrument), and a microsyringe pump (Eicom) were used. The animal models were housed in cages maintained under constant temperature and humidity conditions with a 12-h light/dark cycle and were given water and food ad libitum over the entire experimental period.

For a comparative experiment, pGFP-C-shLenti-non-targeting shRNA control vector (TR30021) expressing only GFP in the animal models of cognitive dysfunction (APP/PS1) (10 months old) and the normal control group (WT) (10 months old) was injected into the striatum according to the same procedure as above.

Three Groups of Experimental Animals

Group 1 (APP/PS1+MeCP2+GFP): 10-month-old APP/PS1 mice genetically mutated to overproduce beta-amyloid (Aβ, β amyloid)+pGFP-C-shLenti-MeCP2 shRNA vector (ORIGENE) injected into the striatum Group 2 (APP/PS1+GFP): 10-month-old APP/PS1 mice genetically mutated to overproduce beta-amyloid (Aβ, β amyloid)+pGFP-C-shLenti-non-targeting shRNA control vector (TR30021) injected into the striatum Group 3 (WT+GFP): 6-month or 10-month-old normal laboratory animals without genetic mutation+pGFP-C-shLenti-non-targeting shRNA control vector (TR30021) injected into the striatum Experimental Example 3. Analysis of Clinical Symptoms in Cognitive Dysfunction Animal Models (6 Months Old)

3-1. Analysis for Beta-Amyloid Plaque Formation

The following experiment was conducted to compare whether beta-amyloid plaques were formed in brain tissue sections from the APP/PS1 cognitive dysfunction animal models (6 months old) and the normal control group animal models (6 months old) established in Experimental Example 1.

The APP/PS1 cognitive dysfunction animal models and the normal control animal models were intraperitoneally injected with ketamine and xylazine for anesthesia, perfused with 4% paraformaldehyde (0.1 M phosphate buffer, pH 7.4), and fixed.

The brain was taken out, immersed in PBS containing 20% sucrose for one day, and sliced into continuous coronal sections with a thickness of 40 μm using a freezing microtome. The tissue sections were stained with thioflavin S (Sigma-Aldrich) solution for 8 min. For observation, the stained sections were washed once with 100% ethanol and twice with 80% ethanol/water and shaken in distilled water for 10 min (Tasai et al., JEM, 2007). The immunolabeled slides were quantified and analyzed using a Leica DMR microscope (Leica Microsystems, Wetzlar, Germany) with a CoolSNAP camera (Princeton, Trenton, NJ, USA).

3-2. Y-Maze Test (YMT)

A Y-maze with three arms (42×3×12 cm) at angles of 120° was prepared. Experimental animals were placed at the ends of the three arms of the Y-maze and allowed to freely explore the Y-maze for 8 min. The exploration was observed using a computer with Ethovision system (Noldus IT b.v., Netherlands). The three arms were designated as A, B, and C, respectively. Every entry was counted as valid only when all four limbs were placed in the arm. The entry to the three different arms in succession was defined as spontaneous alternation behavior. The alternation score (%) was calculated by: Alternation (%)=[(Number of alternations)/(Total number of entries−2)]×100

3-3. Passive Avoidance Test

Figure 3:
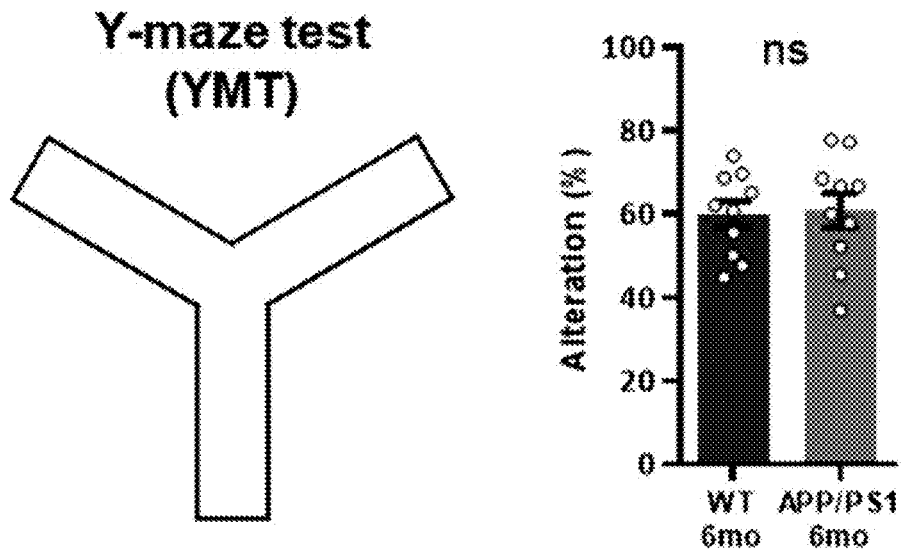
FIG. 3 shows the results of a Y-maze test (YMT) for APP/PS1 cognitive dysfunction animal models (6 months old) and normal control animal models (6 months old) in Experimental Example 1.

The passive avoidance test apparatus consisted of two divided compartments: an illuminated compartment and a dark compartment. The floor was made of wire mesh. During training, each experimental animal was initially placed in the illuminated compartment. Once the animal entered the dark compartment, the door was closed and a foot shock (0.1 mA for 3 sec) was applied. One day after training, the animal was placed again in the illuminated compartment. The time until the animal entered the dark compartment was measured. The maximum time was set to 600 sec (FIG. 3). The passive avoidance test was conducted to evaluate spatial learning and memory.

3-4. Three-Chamber Test (3CT)

A 3-chamber test (3CT) was conducted to investigate negative symptoms of early dementia. 3CT is the most widely used behavioral test to investigate the sociability of mice. Specifically, a chamber structure consisting of three consecutive chambers separated by transparent walls was prepared. Each experimental animal was placed in EthoVision XT 11.5 (Noldus, Netherlands) in the middle chamber. A live mouse (S1) was placed in one of the two end chambers and an inanimate object (0) was placed in the other chamber. Alternatively, a familiar mouse (S1) was placed in one of the end chambers and a novel mouse (S2) was placed in the other chamber. The chamber where the experimental mouse stayed for a longer time was more deeply colored in red. The test was conducted for 10 min.

3-5. Statistics

All data were expressed as mean (S.E.M). Comparisons of group means were performed using Student's t-test. Values of $p<0.05^*$, $p<0.01^{}$, and $p<0.001^{*}$ were considered to be statistically different.

Figure 2:
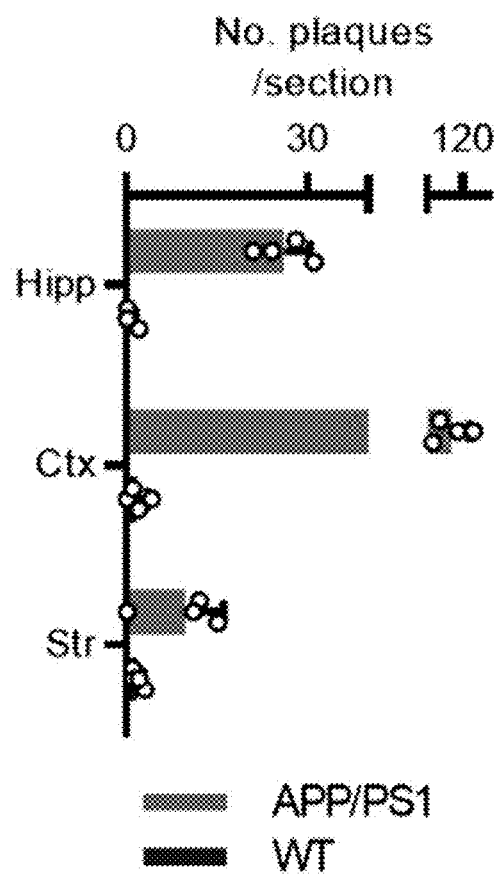
FIG. 2 shows the numbers of beta-amyloid plaques measured in different brain tissue sections (Str: striatum; Hipp: hippocampus; Ctx: cerebral cortex) from an APP/PS1 cognitive dysfunction animal model (6 months old) and a normal control animal model (6 months old) in Experimental Example 1.

FIG. 1 shows two-photon microscopy images of the brain tissue sections from the APP/PS1 cognitive dysfunction animal model (6 months old) and the normal control animal model (6 months old) established in Experimental Example 1 after staining with thioflavin S. FIG. 2 shows the numbers of beta-amyloid plaques measured in different brain tissue sections (Str: striatum; Hipp: hippocampus; Ctx: cerebral cortex) from the APP/PS1 cognitive dysfunction animal model (6 months old) and the normal control animal model (6 months old) in Experimental Example 1.

As shown in FIG. 1, no beta-amyloid plaques were observed in the normal control animal model but a large number of beta-amyloid plaques were observed in the APP/PS1 cognitive dysfunction animal model.

As shown in FIG. 2, beta-amyloid plaques were observed only in the APP/PS1 cognitive dysfunction animal model, demonstrating significant overproduction of beta-amyloid in the APP/PS1 cognitive dysfunction animal model.

Figure 4:
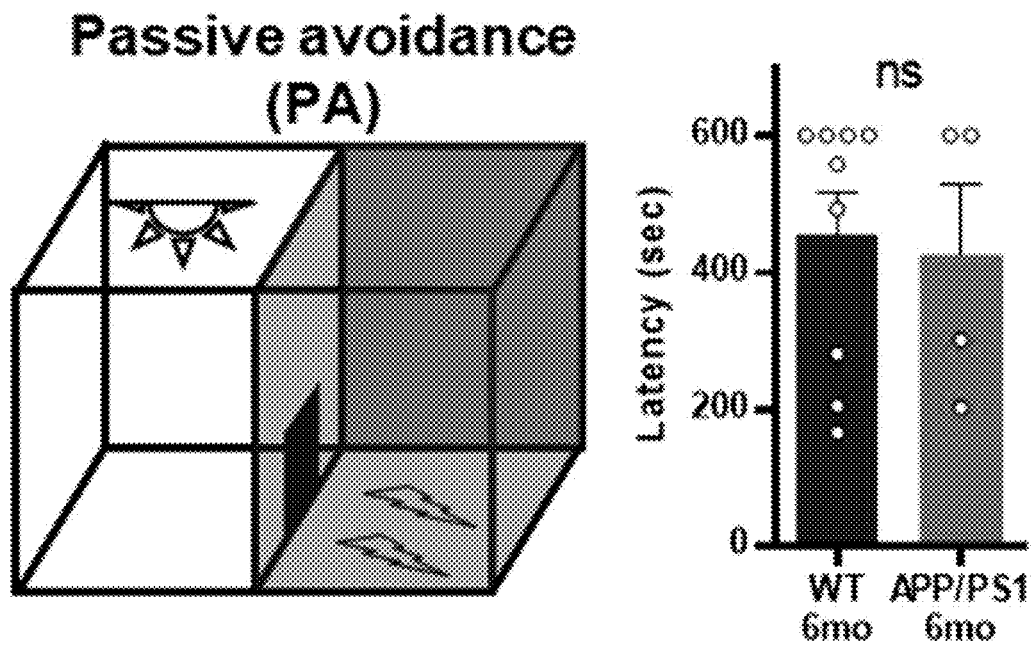
FIG. 4 shows the results of a passive avoidance test for APP/PS1 cognitive dysfunction animal models (6 months old) and normal control animal models (6 months old) in Experimental Example 1.

FIG. 3 shows the results of the Y-maze test (YMT) for the APP/PS1 cognitive dysfunction animal models (6 months old) and the normal control animal models (6 months old) in Experimental Example 1. FIG. 4 shows the results of the passive avoidance test for the APP/PS1 cognitive dysfunction animal models (6 months old) and the normal control animal models (6 months old) in Experimental Example 1.

As shown in FIGS. 3 and 4, changes in the cognitive function of the normal control animal models and the APP/PS1 cognitive dysfunction animal models were at similar levels. From 10-12 months after the onset of cognitive dysfunction, distinct symptoms of cognitive dysfunction are manifested. However, it is known that distinct symptoms of cognitive dysfunction are not manifested up to ~6 months after the onset of cognitive dysfunction, which corresponds to the early stage of the disease. This was also confirmed in this experiment. However, once cognitive dysfunction develops, changes in various symptoms, including memory decline, appear even in the early stage of cognitive dysfunction. Therefore, the following tests were conducted to determine whether psychotic changes, including changes in cognitive function, appeared in the early stage of the onset of cognitive dysfunction.

FIGS. 5 and 6 show the results of the 3-chamber test (3CT) for the APP/PS1 cognitive dysfunction animal models (6 months old) and the normal control animal models (6 months old) in Experimental Example 1. Specifically, FIG. 5 shows the degrees of interest of the APP/PS1 cognitive dysfunction animal models (6 months old) and the normal control animal models (6 months old) in an inanimate object (0) and a live mouse (S1) and FIG. 6 shows the degrees of interest of the APP/PS1 cognitive dysfunction animal models (6 months old) and the normal control animal models (6 months old) in a familiar mouse (S1) and a novel mouse (S2).

As shown in FIGS. 5 and 6, the APP/PS1 cognitive dysfunction animal models did not show a preference for the novel mouse (S2) compared to the familiar mouse (S1), indicating that their sociability was lower than that of the normal control animal models.

The normal control animal models showed higher interest (higher sociability) in the novel mouse (S2) than the familiar mouse (S1), whereas the APP/PS1 cognitive dysfunction animal models lost their preference for both mice, indicating their significantly lower sociality.

Taken together, the APP/PS1 cognitive dysfunction animal models (6 months old) had many beta-amyloid plaques but were not different in cognitive function from the normal control animal models because they were in the early stage of the onset of cognitive dysfunction. However, the APP/PS1 cognitive dysfunction animal models showed abnormal behaviors representing psychotic symptoms accompanying cognitive dysfunction and had high social deficits.

Experimental Example 4. Analysis of Effects in Cognitive Dysfunction Animal Models (10 Months Old)

In this example, the 10-month-old APP/PS1 cognitive dysfunction animal models established in the previous experimental example were used. Finally, the following tests were conducted using the experimental animals of Groups 1-3 in Experimental Example 2.

4-1. Immunohistochemical Staining

Striatal tissues isolated from the experimental animals of Groups 1-3 in Experimental Example 2 were washed with PBS, fixed in 4% formalin solution for 20 min, incubated in a 0.1% triton X-100/PBS solution for 10 min, washed with PBS, and blocked with a 0.1% skim milk (Fluka biochemika, cat. #70166, Switzerland)/PBS solution for 10 min to remove non-specific binding of antibodies. Monoclonal mouse primary antibodies anti-neuronal nuclei (NeuN, 1:100, Chemicon, cat. #MAB377B, USA) were incubated at room temperature for 1 h and washed 3 times with PBS. Goat anti-mouse Alexa Fluor 594 (Molecular proves, cat. #A11005, USA) secondary antibody was incubated at room temperature for 1 h. After double staining with 4',6'-diamino-2-phenylindole (DAPI, Sigma-Aldrich, USA), the staining results were observed with a fluorescence microscope (Eclipse TE 200, Nikon, Japan).

4-2. Analysis for Beta-Amyloid Plaque Formation

The following experiment was conducted to compare whether beta-amyloid plaques were formed in brain tissue sections from the experimental animals of Groups 1-3 in Experimental Example 2.

The experimental animals of Groups 1-3 were intraperitoneally injected with ketamine and xylazine for anesthesia, perfused with 4% paraformaldehyde (0.1 M phosphate buffer, pH 7.4), and fixed. The brain was taken out, immersed in PBS containing 20% sucrose for one day, and sliced into continuous coronal sections with a thickness of 40 µm using a freezing microtome. The tissue sections were stained with thioflavin S (Sigma-Aldrich) solution for 8 min. For observation, the stained sections were washed once with 100% ethanol and twice with 80% ethanol/water and shaken in distilled water for 10 min (Tasai et al., JEM, 2007). The immunolabeled slides were quantified and analyzed using a Leica DMR microscope (Leica Microsystems, Wetzlar, Germany) with a CoolSNAP camera (Princeton, Trenton, NJ, USA).

4-3. Y-Maze Test (YMT)

A Y-maze with three arms (42×3×12 cm) at angles of 120° was prepared. Experimental animals were placed at the ends of the three arms of the Y-maze and allowed to freely explore the Y-maze for 8 min. The exploration was observed using a computer with Ethovision system (Noldus IT b.v., Netherlands). The three arms were designated as A, B, and C, respectively. Every entry was counted as valid only when all four limbs were placed in the arm. The entry to the three different arms in succession was defined as spontaneous alternation behavior. The alternation score (%) was calculated by: Alternation (%)=[(Number of alternations)/(Total number of entries−2)]×100

4-4. Passive Avoidance Test

The passive avoidance test apparatus consisted of two divided compartments: an illuminated compartment and a dark compartment. The floor was made of wire mesh. During training, each experimental animal was initially placed in the illuminated compartment. Once the animal entered the dark compartment, the door was closed and a foot shock (0.1 mA for 3 sec) was applied. One day after training, the animal was placed again in the illuminated compartment. The time until the animal entered the dark compartment was measured. The maximum time was set to 600 sec (FIG. 3). The passive avoidance test was conducted to evaluate spatial learning and memory.

4-5. Three-Chamber Test (3CT)

A 3-chamber test (3CT) was conducted to investigate negative symptoms of early dementia. 3CT is the most widely used behavioral test to investigate the sociability of mice. Specifically, a chamber structure consisting of three consecutive chambers separated by transparent walls was prepared. Each experimental animal was placed in EthoVision XT 11.5 (Noldus, Netherlands) in the middle chamber. A live mouse (S1) was placed in one of the two end chambers and an inanimate object (S) was placed in the other chamber. Alternatively, a familiar mouse (S1) was placed in one of the end chambers and a novel mouse (S2) was placed in the other chamber. The chamber where the experimental mouse stayed for a longer time was more deeply colored in red. The test was conducted for 10 min.

4-6. Statistics

All data were expressed as mean (S.E.M). Comparisons of group means were performed using Student's t-test and one-way ANOVA test. Values of $p<0.05*$, $p<0.01$, and $p<0.001*$ were considered to be statistically different.

Figure 7:
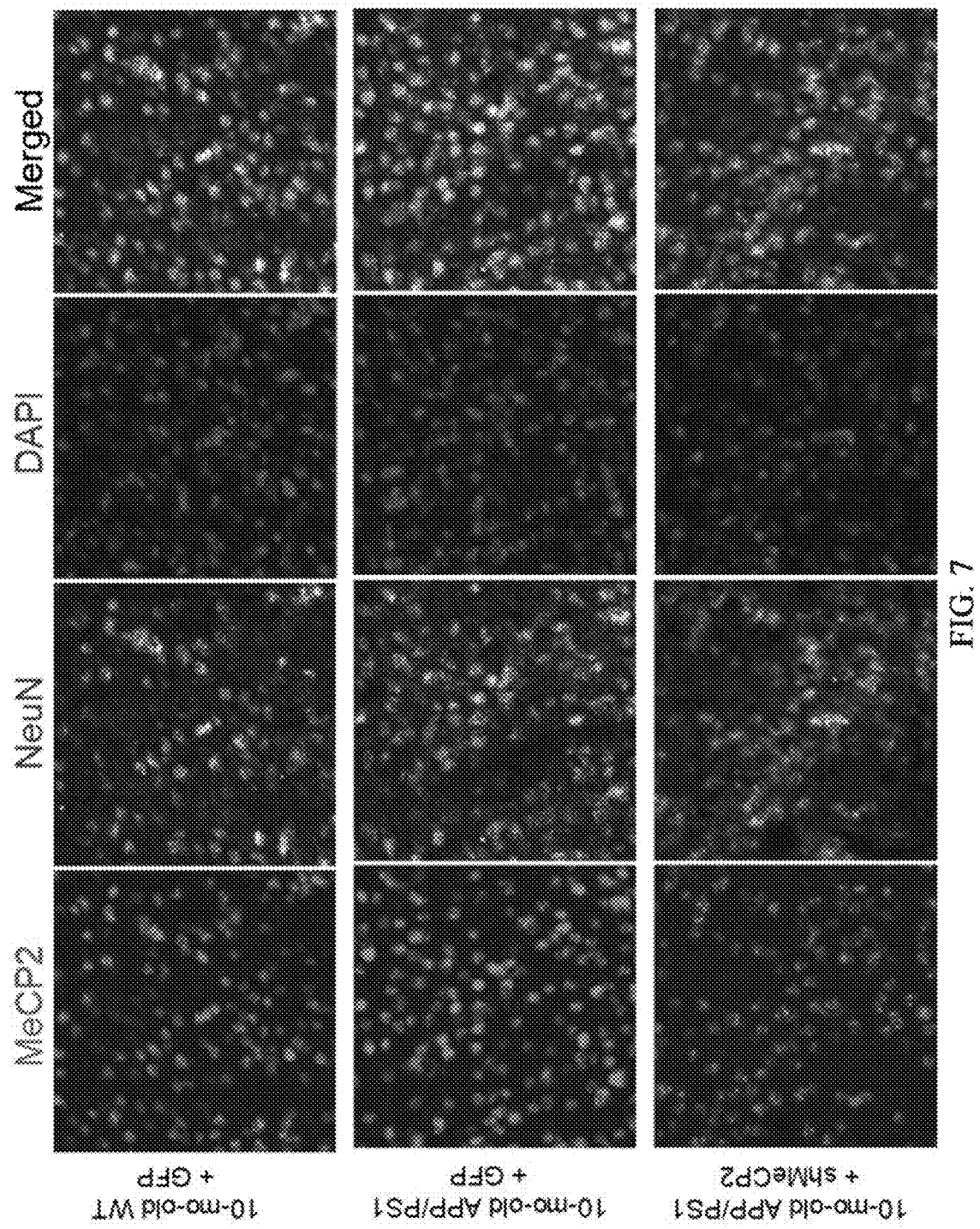
FIG. 7 shows the results of immunohistochemical staining for experimental animals of Groups 1-3 in Experimental Example 2.

FIG. 7 shows the results of immunohistochemical staining for the experimental animals of Groups 1-3 in Experimental Example 2. As shown in FIG. 7, clear differences were observed in the three groups of 10-month-old experimental animals with cognitive dysfunction. Specifically, the expression of MeCP2 in the cognitive dysfunction animal model (APP/PS1+GFP) was significantly higher than that in the normal control group (WT+GFP) but the expression of MeCP2 in the MeCP2-inhibited group (APP/PS1+MeCP2+GFP) was reduced to a lower level than that in the normal control group (WT+GFP).

Figure 8:
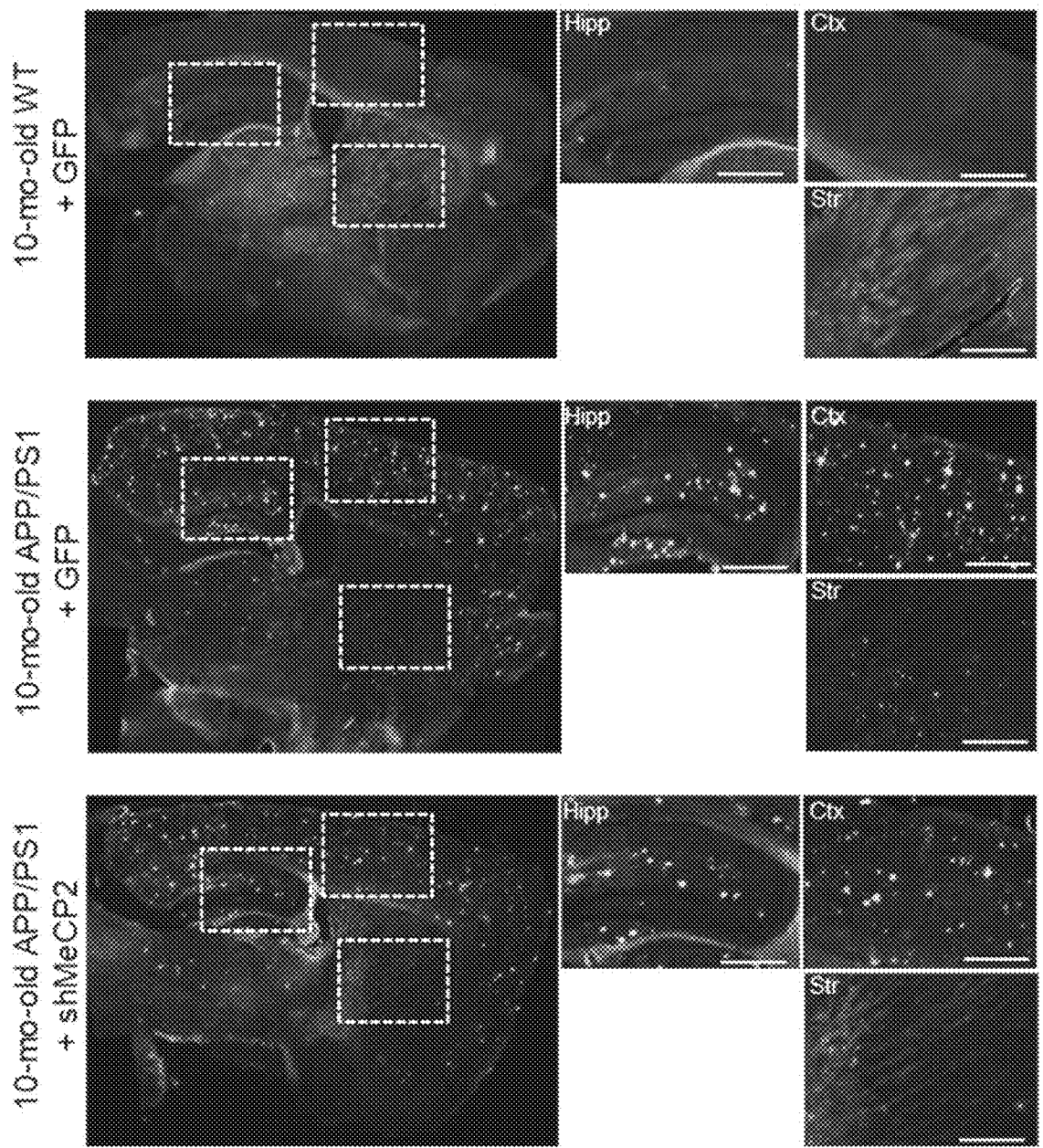
FIG. 8 shows two-photon microscopy images of brain tissue sections from experimental animals of Groups 1-3 in Experimental Example 2 after staining with thioflavin S.
Figure 9:
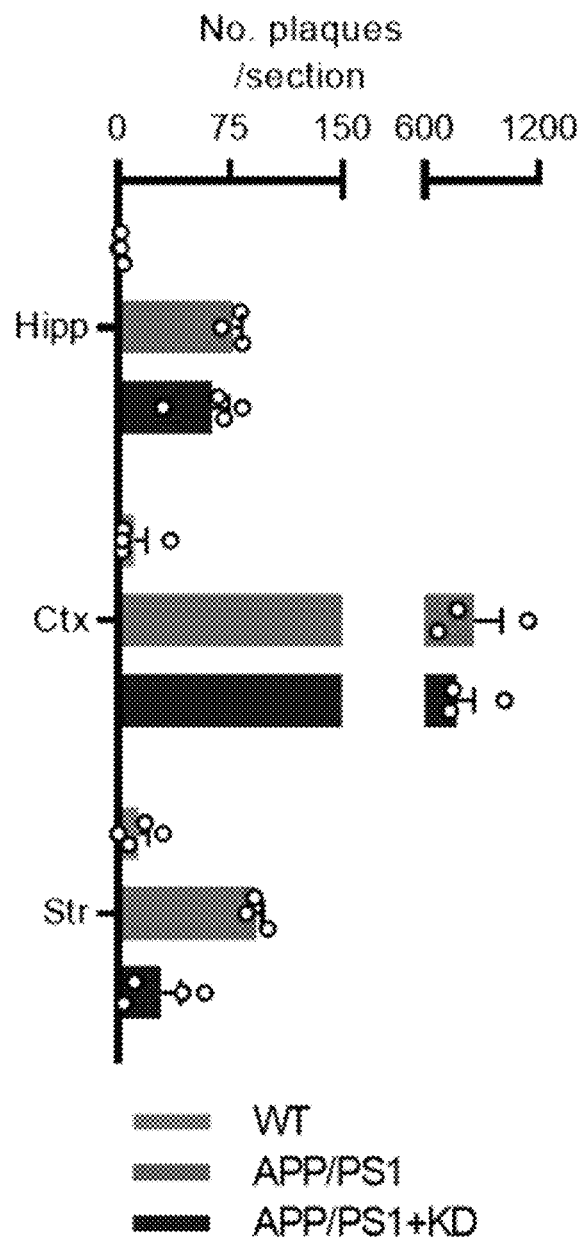
FIG. 9 shows the numbers of beta-amyloid plaques measured in different brain tissue sections (Str: striatum; Hipp: hippocampus; Ctx: cerebral cortex) from experimental animals of Groups 1-3 in Experimental Example 2.

FIG. 8 shows two-photon microscopy images of the brain tissue sections from the experimental animals of Groups 1-3 in Experimental Example 2 after staining with thioflavin S. FIG. 9 shows the numbers of beta-amyloid plaques measured in different brain tissue sections (Str: striatum; Hipp: hippocampus; Ctx: cerebral cortex) from the experimental animals of Groups 1-3 in Experimental Example 2.

As shown in FIGS. 8 and 9, the number of beta-amyloid plaques in the cognitive dysfunction animal model (APP/PS1+GFP) was significantly increased than that in the normal control group (WT+GFP) and the number of beta-amyloid plaques in the MeCP2-inhibited group (APP/PS1+MeCP2+GFP) was significantly increased than that in the normal control group (WT+GFP). These results indicate that the inhibitory effect on MeCP2 expression does not lead to a significant difference in beta-amyloid plaque formation.

Figure 10:
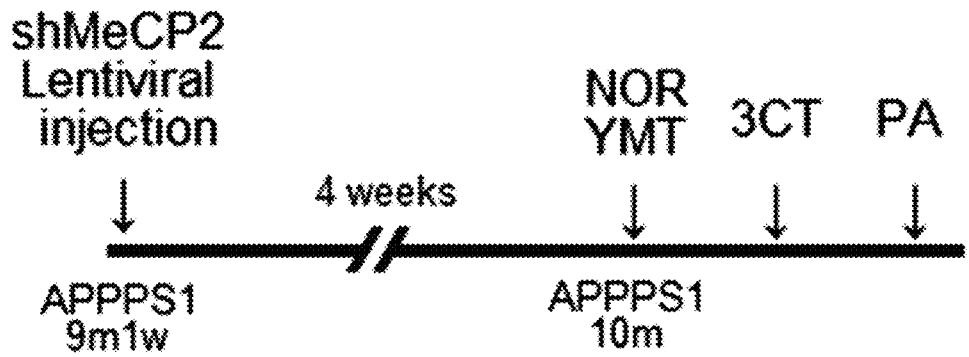
FIG. 10 is an experimental design for experimental animals of Groups 1-3 in Experimental Example 2.
Figure 11:
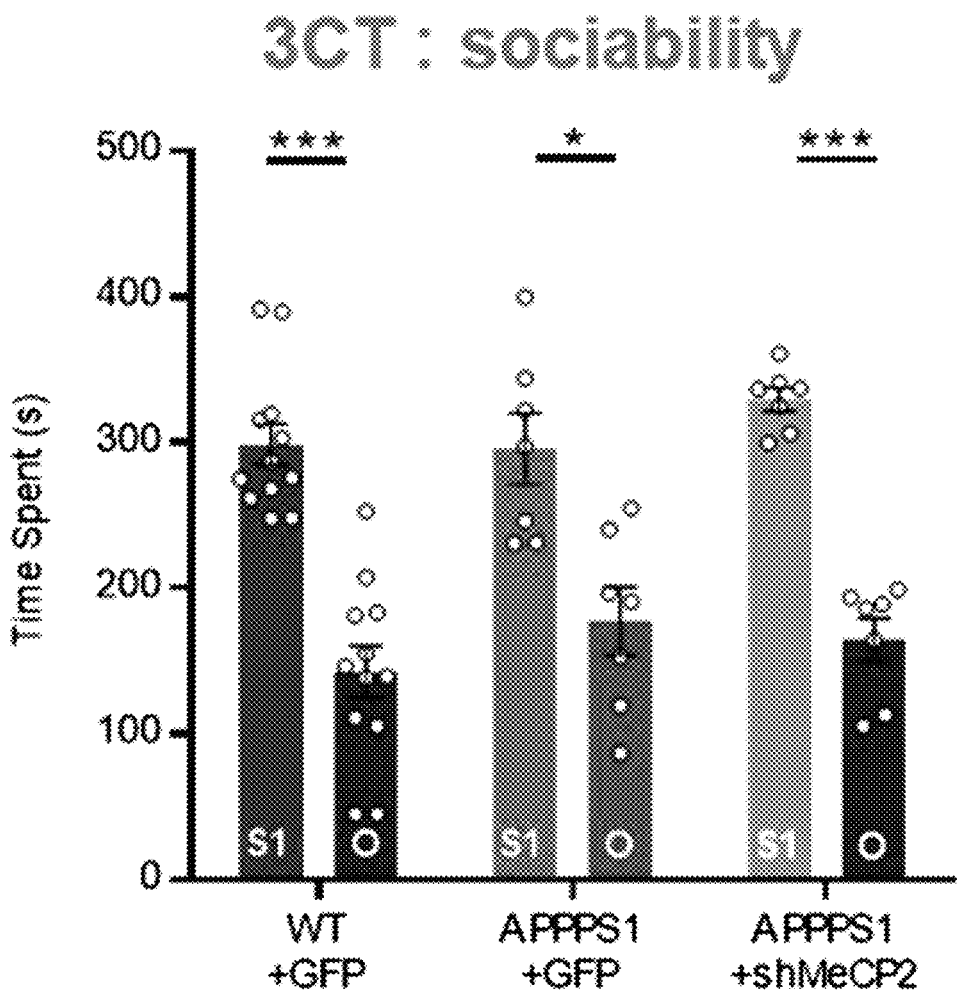
FIGS. 11 and 12 show the results of a 3-chamber test (3CT) for experimental animals of Groups 1-3 in Experimental Example 2. Specifically.
Figure 12:
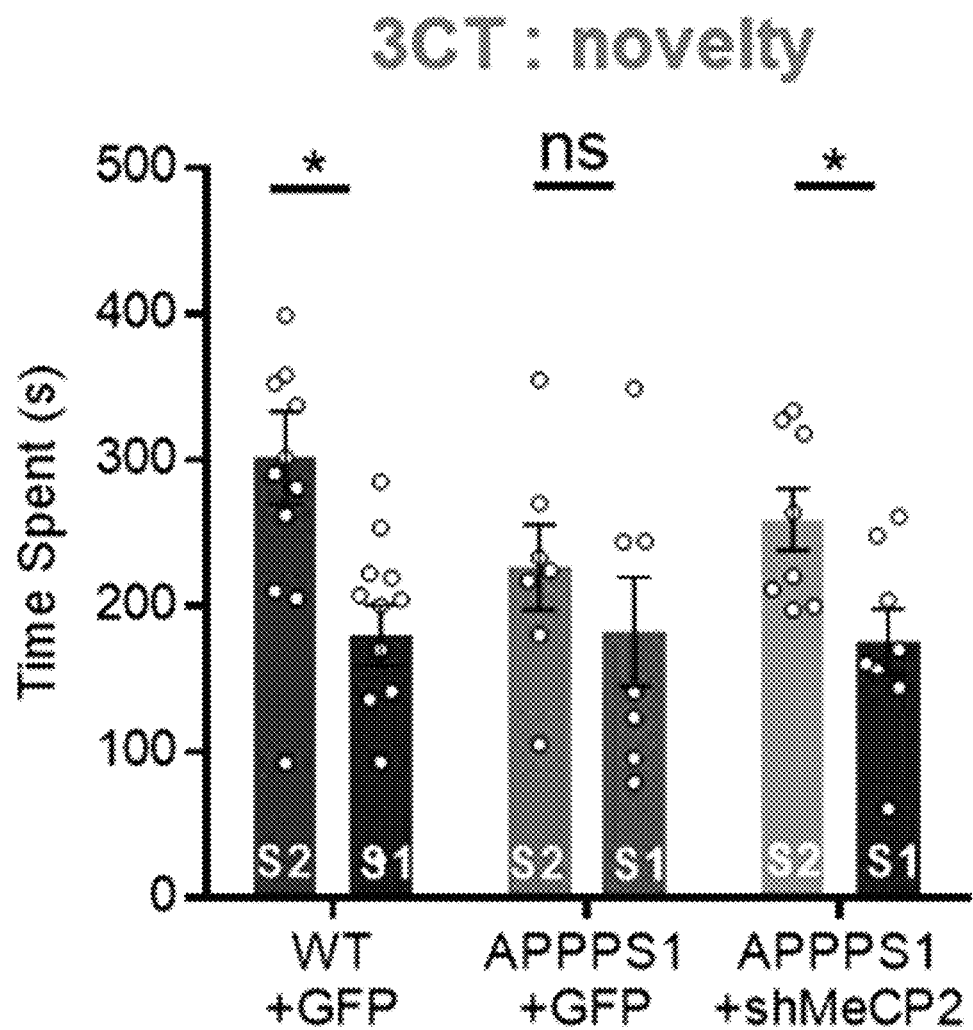

FIG. 10 is an experimental design for the experimental animals of Groups 1-3 in Experimental Example 2. FIGS. 11 and 12 show the results of the 3-chamber test (3CT) for the experimental animals of Groups 1-3 in Experimental Example 2. Specifically, FIG. 11 shows the degrees of interest of the experimental animals of Groups 1-3 in an inanimate object (0) and a live mouse (S1) in Experimental Example 2 and FIG. 12 shows the degrees of interest of experimental animals of Groups 1-3 in Experimental Example 2 in a familiar mouse (S1) and a novel mouse (S2).

As shown in FIGS. 11 and 12, the cognitive dysfunction animal models (APP/PS1+GFP) did not show a preference for the novel mouse (S2) compared to the familiar mouse (S1), indicating that their sociability was lower than that of the normal control animal models. The sociability of the MeCP2-inhibited group (APP/PS1+MeCP2+GFP) was restored to a level similar to that of the normal control group (WT+GFP).

The normal control group (WT+GFP) showed higher interest (higher sociability) in the novel mouse (S2) than the familiar mouse (S1), whereas the APP/PS1 cognitive dysfunction animal models lost their preference for both mice, indicating their significantly lower sociability. However, the knockdown of MeCP2 (APP/PS1+MeCP2+GFP) was found to restore sociality (abnormal behavior) to a level similar to that of the normal control group (WT+GFP). Taken together, the results of behavioral characteristics of the APP/PS1 cognitive dysfunction animal models indicate that the APP/PS1 cognitive dysfunction animal models have severe depression and anxiety symptoms compared to the normal control group.

In summary, the sociabilities (abnormal behaviors; depression and anxiety) of both 6- and 10-month-old APP/PS1 cognitive dysfunction animal models were reduced due to beta-amyloid plaque formation. In addition, the inhibition of MeCP2 expression did not result in a decrease in the number of beta-amyloid plaques but was effective in restoring the sociabilities (abnormal behaviors; depression and anxiety) to normal levels.

Figure 13:
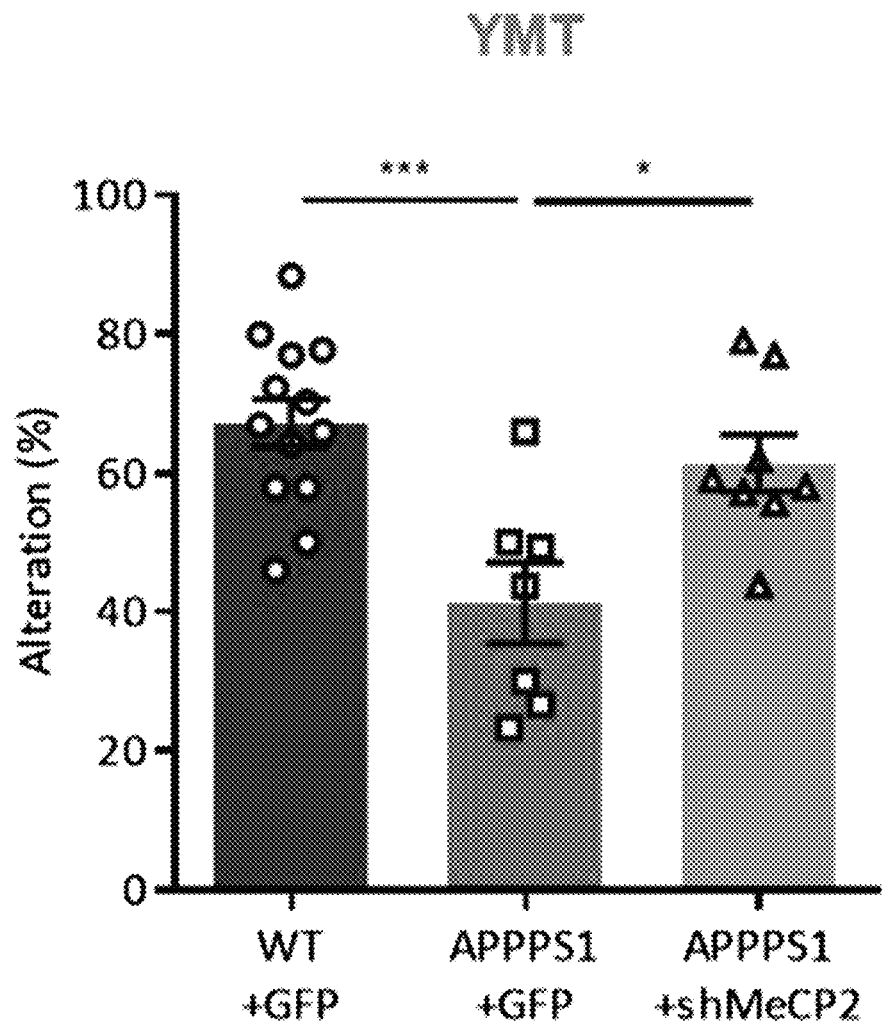
FIG. 13 shows the results of a Y-maze test (YMT) for experimental animals of Groups 1-3 in Experimental Example 2.
Figure 14:
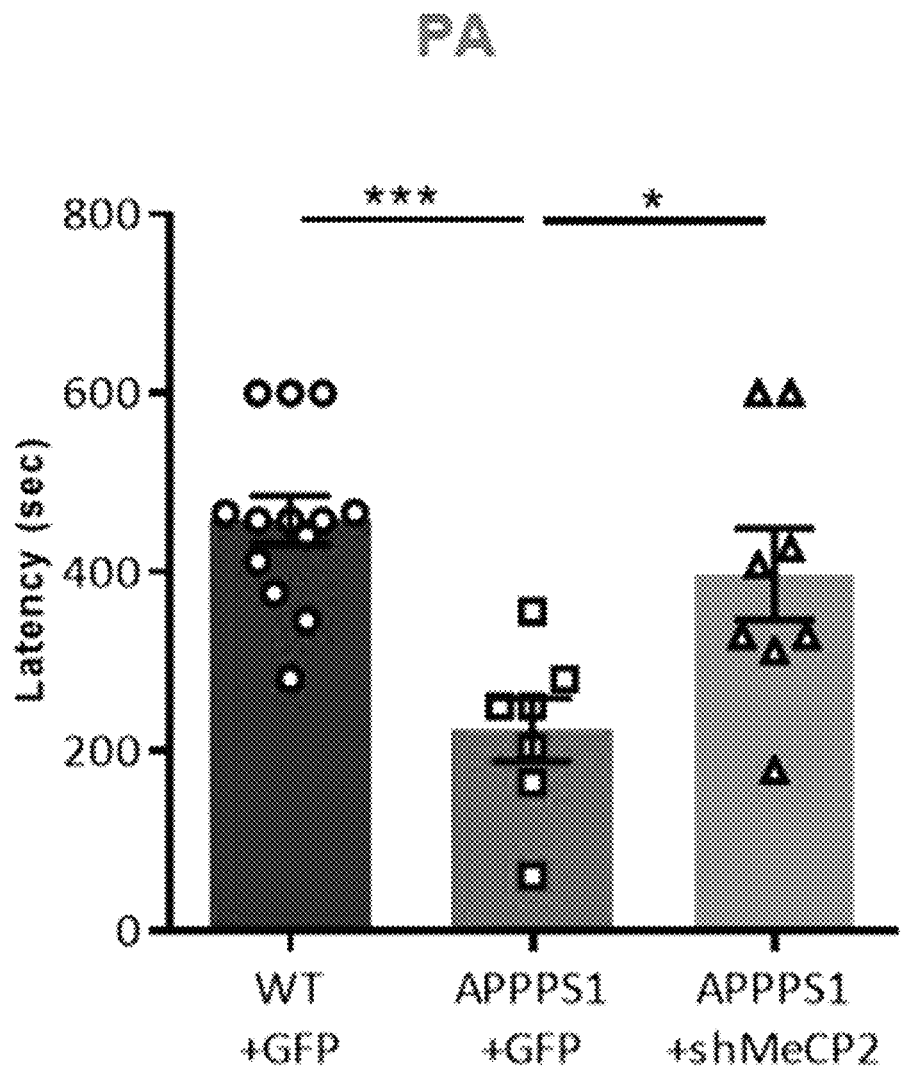
FIG. 14 shows the results of a passive avoidance test for experimental animals of Groups 1-3 in Experimental Example 2.

FIG. 13 shows the results of the Y-maze test (YMT) for the experimental animals of Groups 1-3 in Experimental Example 2. FIG. 14 shows the results of the passive avoidance test for the experimental animals of Groups 1-3 in Experimental Example 2.

As shown in FIGS. 13 and 14, the cognitive functions of the cognitive dysfunction animal models (APP/PS1+GFP)

were significantly deteriorated compared to those of the normal control group (WT+GFP). Distinct symptoms of cognitive dysfunction were manifested in the 10-12-month-old mice, unlike in the 6-month-old mice. The cognitive functions were significantly better recovered in the MeCP2-inhibited group (APP/PS1+MeCP2+GFP) than in the cognitive dysfunction animal models (APP/PS1+GFP). The shRNA against MeCP2 was found to be effective in restoring not only sociality (abnormal behavior) but also cognitive functions.

Taken together, the shRNA against MeCP2 targets genes other than MeCP2 and mechanisms other than the formation of beta-amyloid plaques, which has been reported as a main cause of dementia, to restore the neuronal activity of the striatum, contributing to ameliorating memory decline and psychotic symptoms caused by the development of cognitive dysfunction.

Experimental Example 5. Confirmation of Effect of the shRNA Against MeCP2 on Neuronal Action Potential Restoration In this example, the effect of treatment with the shRNA against MeCP2 on neuronal action potential was investigated. To this end, neuronal action potentials were measured to compare the degrees of neuronal activation. As shown in FIG. 15, early hippocampal neurons from the experimental animals of Groups 1-3 in Experimental Example 2 were cultured in vitro on a microelectrode array (MEA) and stimulation currents were applied to induce responses of the neurons. The stimulation currents were cathodic phase pulses (negative-positive) whose magnitudes were 125-1000 nA. A total of 30 repetitive pulses at the same magnitude were applied to the cells. The inter-pulse intervals were 1 sec. Cellular responses to the electrical pulses were read through the microelectrodes, amplified using a multichannel amplifier (Multichannel systems), and visualized and quantified using the MC rack program. For quantification, the average firing rate of the stored neural signals was calculated in time units (500 msec bin), the firing rate for 10 sec before laser irradiation was subtracted from the average firing rate for 10 sec during laser irradiation, and this value was divided by the average firing rate for 10 sec before laser irradiation to calculate a variation.

Figure 17:
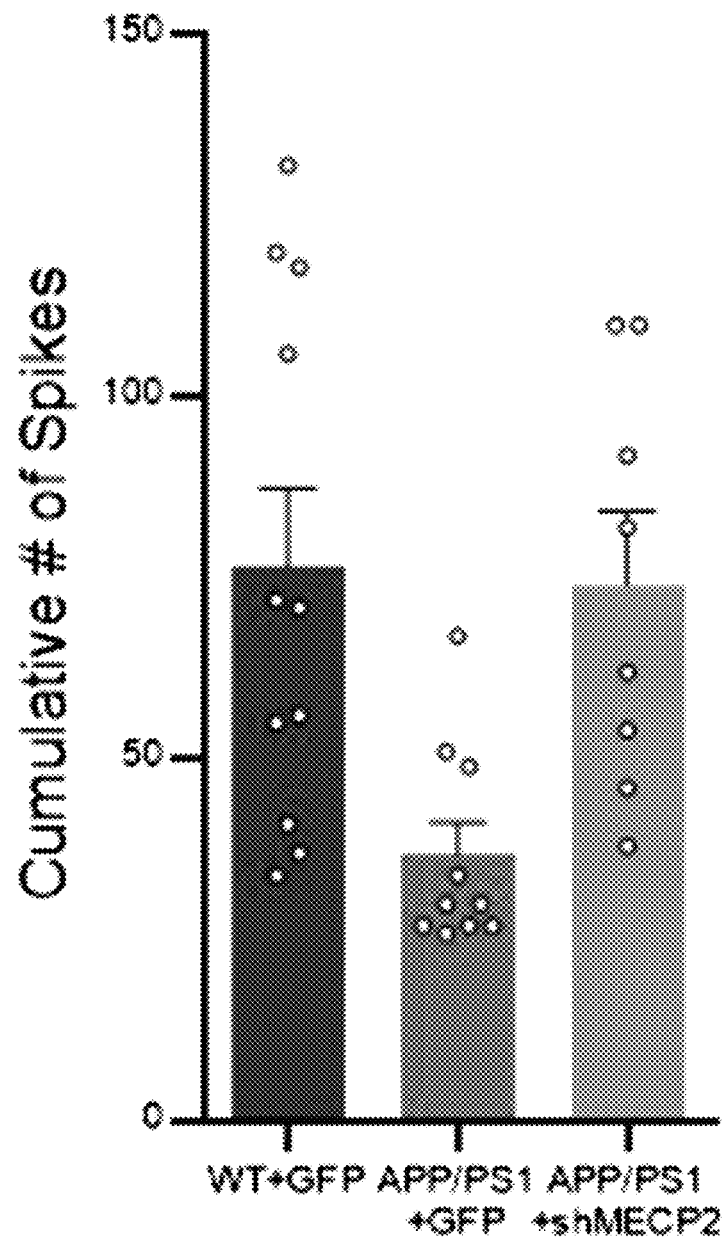
FIG. 17 shows changes in the cumulative neuronal activity of experimental animals of Groups 1-3 in Experimental Example 2.

Input spikes to the neurons were integrated in the form of neuronal membrane potentials and were fired when the membrane potential reached a certain threshold. As a result, output spikes were sent to neighboring neurons. The cumulative number of the fired spikes was measured. The results are shown in FIG. 17.

All data were expressed as mean (S.E.M). Comparisons of group means were performed using Student's t-test and one-way ANOVA test. Values of $p<0.05$*, $p<0.01$, and $p<0.001$* were considered to be statistically different.

Figure 16:
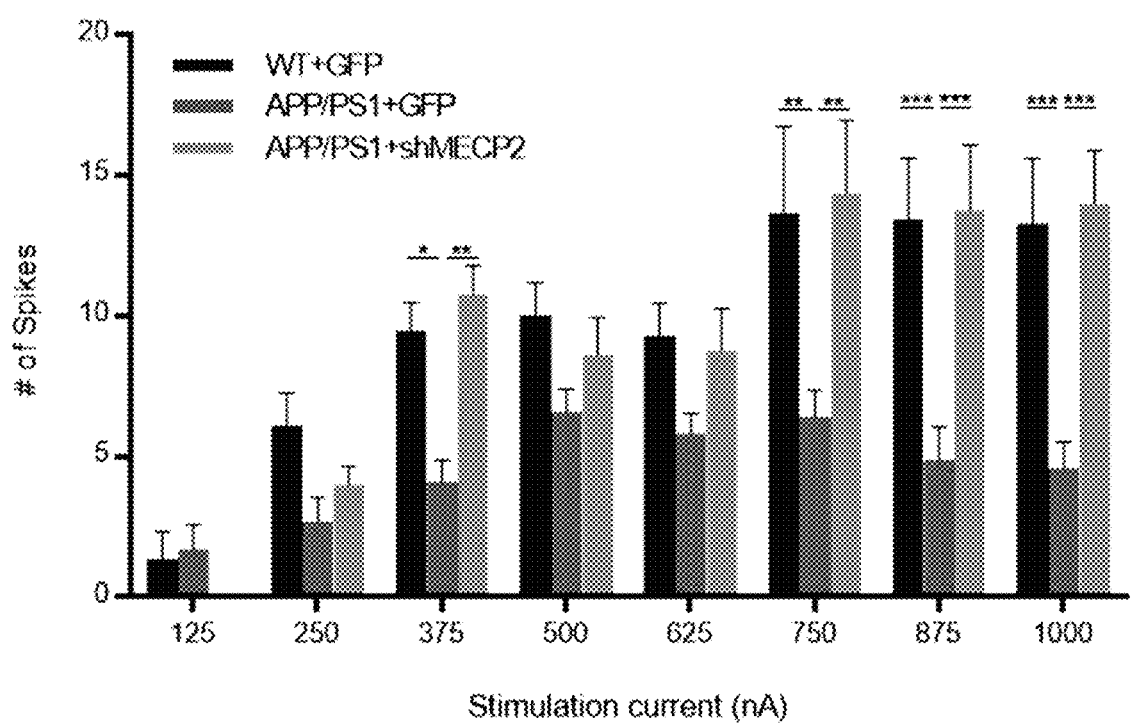
FIG. 16 shows changes in the neuronal activity of experimental animals of Groups 1-3 in Experimental Example 2.
Figure 18:
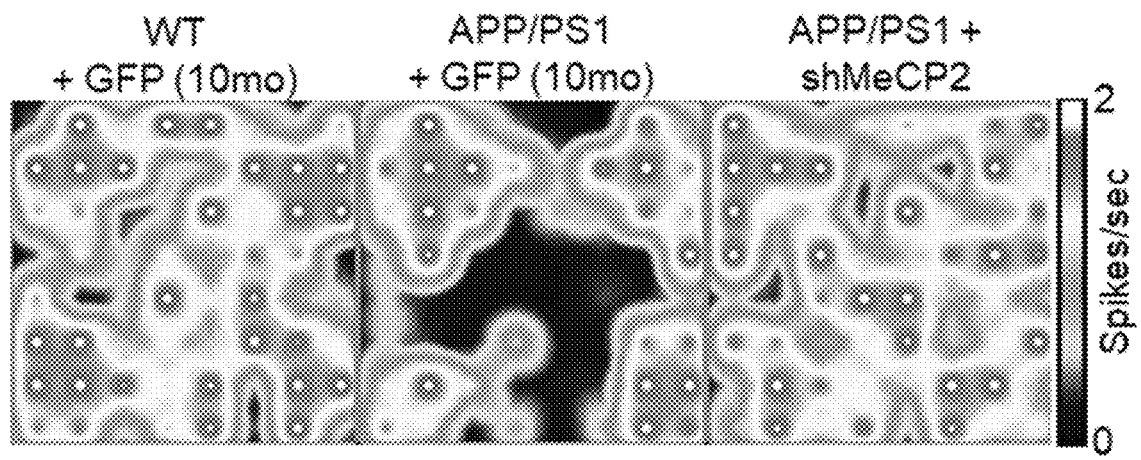
FIG. 18 shows images showing the neuronal activities of experimental animals of Groups 1-3 in Experimental Example 2 on MEA probes.
Figure 19:
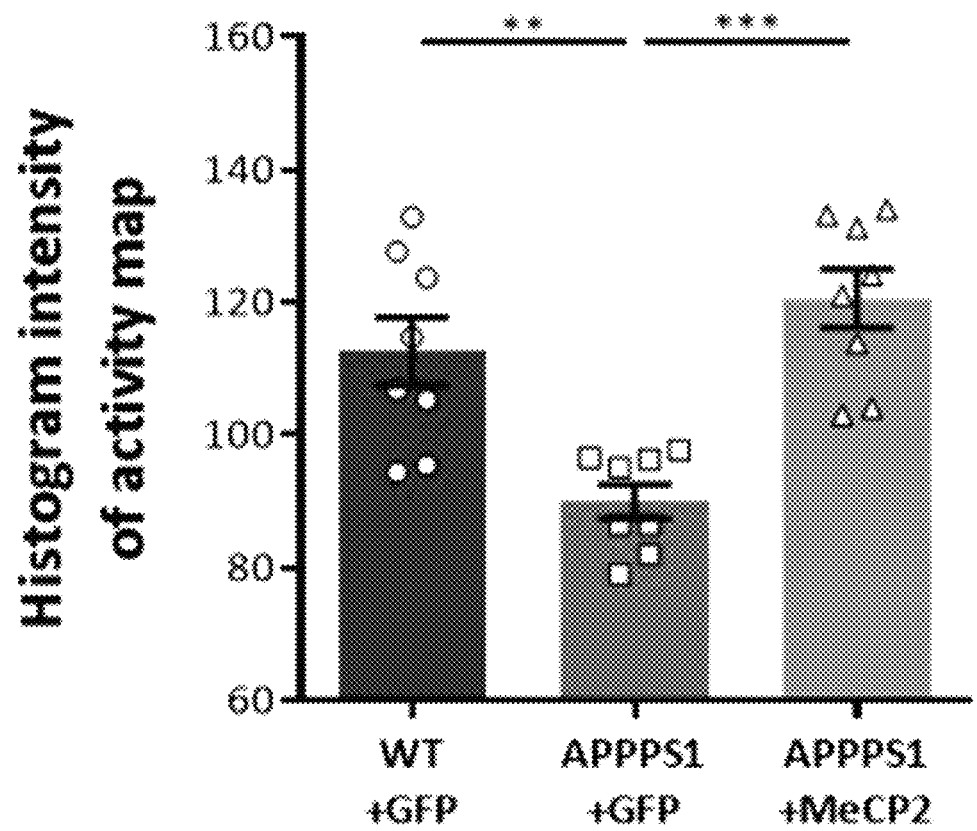
FIG. 19 is a quantification graph of FIG. 18.

FIG. 15 schematically shows the microelectrode array (MEA). FIG. 16 shows changes in the neuronal activity of the experimental animals of Groups 1-3 in Experimental Example 2. FIG. 17 shows changes in the cumulative neuronal activity of the experimental animals of Groups 1-3 in Experimental Example 2. FIG. 18 shows images showing the neuronal activities of the experimental animals of Groups 1-3 in Experimental Example 2 on the MEA probes. FIG. 19 is a quantification graph of FIG. 18.

As shown in FIGS. 15 to 19, the action potentials of the cognitive dysfunction animal models (APP/PS1+GFP) (red bars) were significantly lower than those of the normal control group (WT+GFP). In contrast, the action potentials of the MeCP2-inhibited group (APP/PS1+MeCP2+GFP) were restored to the levels of the normal control group (WT+GFP).

That is, the administration of the shRNA against MeCP2 significantly and remarkably increased the generation of neuronal action potentials.

Experimental Example 6. Analysis of Expression of Marker Protein (rPS6) for Neuronal Activity by the shRNA Against MeCP2

Striatal tissues isolated from the experimental animals of Groups 1-3 in Experimental Example 2 were washed with PBS, fixed in 4% formalin solution for 20 min, incubated in a 0.1% triton X-100/PBS solution for 10 min, washed with PBS, and blocked with a 0.1% skim milk (Fluka biochemika, cat. #70166, Switzerland)/PBS solution for 10 min to remove non-specific binding of antibodies. Rabbit anti-mouse Phospho-S6 ribosomal protein (Ser235/236) (Clone #D57.2.2E) as a primary antibody was incubated at room temperature for 1 h and washed 3 times with PBS. Goat anti-mouse Alexa Fluor 594 (Molecular proves, cat. #A11005, USA) secondary antibody was incubated at room temperature for 1 h. After double staining with 4',6'-diamino-2-phenylindole (DAPI, Sigma-Aldrich, USA), the staining results were observed with a fluorescence microscope (Eclipse TE 200, Nikon, Japan).

Figure 20:
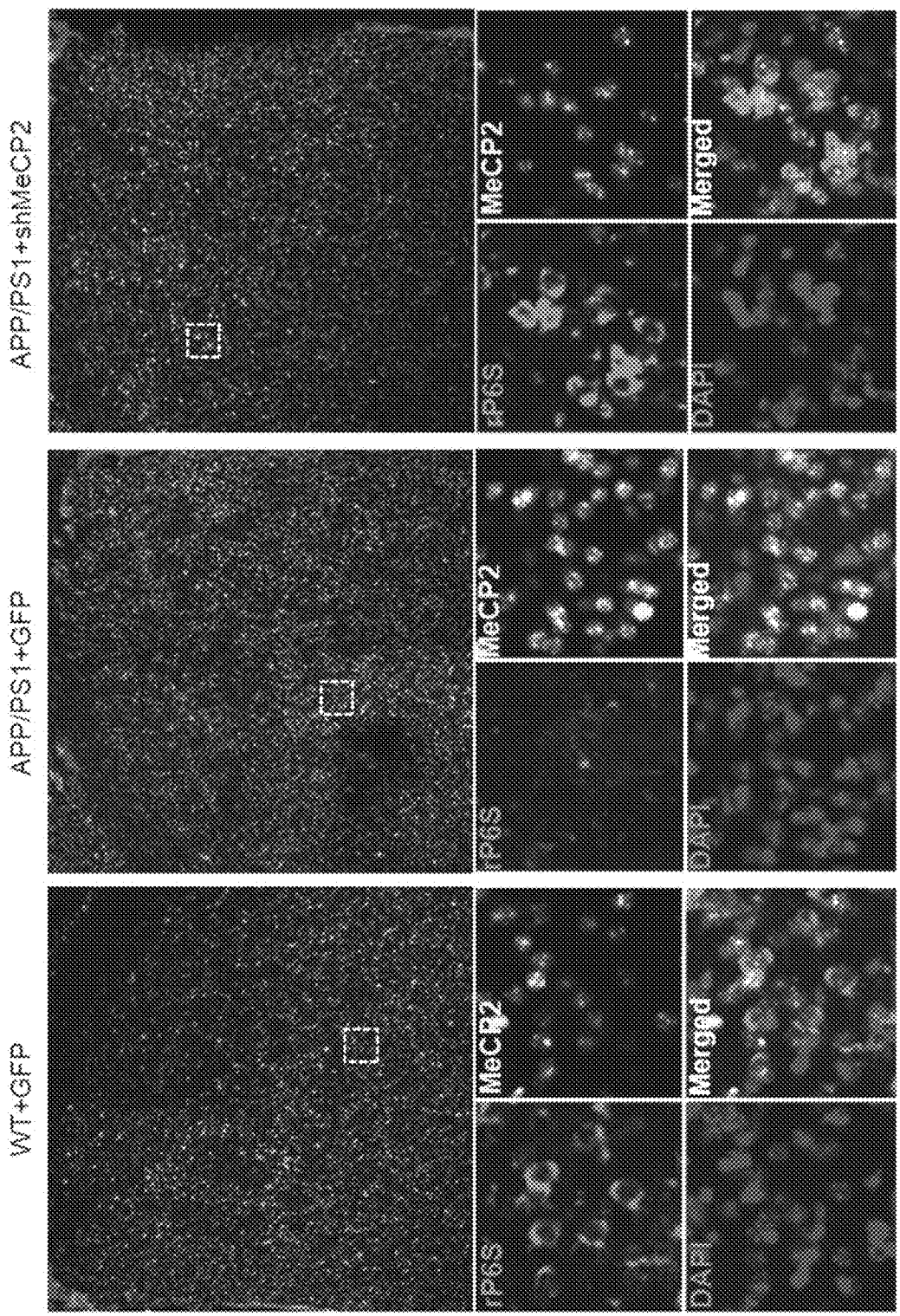
FIG. 20 shows the results of immunohistochemical staining for experimental animals of Groups 1-3 in Experimental Example 2.

FIG. 20 shows the results of immunohistochemical staining for the experimental animals of Groups 1-3 in Experimental Example 2. Specifically, the expression of rPS6 (Ribosomal Protein S6), a marker protein for neuronal activity, in the cognitive dysfunction animal model (APP/PS1+GFP) was greatly reduced. In contrast, the expression of rPS6 (Ribosomal Protein S6) in the MeCP2-inhibited group (APP/PS1+MeCP2+GFP) was increased to a higher level than that in the normal control group (WT+GFP).

That is, the shRNA against MeCP2 has no inhibitory efficacy against beta-amyloid but has the ability to activate neurons in patients suffering from cognitive dysfunction, thus being very effective in preventing, ameliorating, and treating cognitive dysfunction.

What is claimed is:

1. A method for treating Alzheimer's disease, comprising administering to a human or non-human mammal in need of such treatment a pharmaceutical composition comprising an inhibitor of methyl CpG binding protein 2 (MECP2) expression or activity as an active ingredient,
  wherein the inhibitor of MECP2 expression or activity is shRNA that bind complementarily to the MECP2 mRNA or a viral vector containing the shRNA, and
  wherein the shRNA inhibiting MECP2 expression has the sequence set forth in any one of SEQ ID NOS: 3 to 6.

2. The method according to claim 1, wherein the viral vector is selected from the group consisting of retrovirus, adenovirus, adeno-associated virus, herpes simplex virus, lentivirus, and combinations thereof.

3. The method according to claim 1, wherein Alzheimer's disease is accompanied with a psychiatric disorder selected from the group consisting of personality change, delusion, hallucination, mood disorder, sleep disorder, change of appetite, altered sexual behavior, psychosis, aggression, irritability, nervousness, hostility, depression, anxiety disorder, lethargy, and combinations thereof.

\* \* \* \* \*